United States Patent
Michels et al.

(10) Patent No.: US 9,422,263 B2
(45) Date of Patent: *Aug. 23, 2016

(54) FLUORO-SUBSTITUTED 3,5-DICYANO-4-(1H-INDAZOL-5-YL)-2,6-DIMETHYL-1,4-DIHYDROPYRIDINE DERIVATIVES AND METHODS OF USE THEREOF

(75) Inventors: Martin Michels, Köln (DE); Markus Follmann, Wülfrath (DE); Alexandros Vakalopoulos, Hilden (DE); Katja Zimmermann, Düsseldorf (DE); Nicole Teusch, Wülfrath (DE); Mario Lobell, Wuppertal (DE); Donald Bierer, Haan (DE); Karen Engel, Wuppertal (DE); Maria Kissel, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 67 days.

This patent is subject to a terminal disclaimer.

(21) Appl. No.: 13/496,722

(22) PCT Filed: Oct. 1, 2010

(86) PCT No.: PCT/EP2010/064648
§ 371 (c)(1),
(2), (4) Date: Jun. 26, 2012

(87) PCT Pub. No.: WO2011/042368
PCT Pub. Date: Apr. 14, 2011

(65) Prior Publication Data
US 2012/0264785 A1    Oct. 18, 2012

(30) Foreign Application Priority Data
Oct. 6, 2009 (EP) .................................... 09172304

(51) Int. Cl.
*C07D 401/04* (2006.01)
(52) U.S. Cl.
CPC .................................... *C07D 401/04* (2013.01)
(58) Field of Classification Search
CPC .................................................... C07D 404/04
USPC ...................................... 546/275.7; 514/339
See application file for complete search history.

(56) References Cited

U.S. PATENT DOCUMENTS 8,198,456 B2 * 6/2012 Adler et al. ................ 546/275.7

FOREIGN PATENT DOCUMENTS

WO    2008/071451    *    6/2008

OTHER PUBLICATIONS

Purser et al., Fluorine in Medicinal Chemistry, 37(2) Chem. Soc. Rev. 320-330 (2008).*
Yu et al., "Physical characterization of, etc.," PSTT, vl. 1(3), 118-127 (1998).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Jain et al., "Polymorphism in Pharmacy", Indian Drugs, 1986, 23(6) 315-329.*
Guillory (in Brittain ed.), "Polymorphism in Pharmaceutical Solids.," NY: Marcel Dekker, Inc., 1999, 1-2, 125-181, 183-226.*
LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Ouaissi et al., "Rationale for Possible, etc.," Journal of Biomedicine and Biotechnology, 2011, Article: ID 315939, 1-8.*
Golub et al, Science, vol. 286, Oct. 15, 1999, pp. 531-537.*

* cited by examiner

*Primary Examiner* — Patricia L Morris

(57) ABSTRACT

The present invention relates to novel fluoro-substituted 3,5-dicyano-4-(1H-indazol-5-yl)-2,6-dimethyl-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

10 Claims, No Drawings

FLUORO-SUBSTITUTED 3,5-DICYANO-4-(1H-INDAZOL-5-YL)-2,6-DIMETHYL-1,4-DIHYDROPYRIDINE DERIVATIVES AND METHODS OF USE THEREOF

The present invention relates to novel fluoro-substituted 3,5-dicyano-4-(1H-indazol-5-yl)-2,6-dimethyl-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

Cancer is one of the most common widespread diseases. Over 4.4 million people worldwide were diagnosed with breast, colon, ovarian, lung or prostate cancer in 2002, and over 2.5 million people died of these devastating diseases (Globocan 2002 Report, http://www-dep.iarc.fr/globocan/downloads.htm). In the United States alone, over 1.25 million new cases and over 500 000 deaths from cancer were predicted in 2005. The majority of these new cases were expected to be cancers of the colon (~100 000), lung (~170 000), breast (~210 000) and prostate (~230 000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

There are many ways how cancers can arise, which is one of the reasons why their therapy is difficult. One way is the transformation of cells by oncoproteins, which arise from normal cellular proteins by genetic mutations, which results in a non-physiological activation of these proteins. One family of proteins from which a number of oncoproteins derive are tyrosine kinases (e.g. src kinase) and in particular receptor tyrosine kinases (RTKs). In the past two decades, numerous avenues of research have demonstrated the importance of receptor tyrosine kinase (RTK)-mediated signalling in the regulation of mammalian cell growth. Recently, results have been achieved in the clinic with selective small-molecule inhibitors of tyrosine kinases as anti-tumourigenic agents.

The c-Met receptor also is a receptor tyrosine kinase. Its oncogenic potential was identified in the early 1980s, when a mutated Met was isolated from a chemically induced human osteosarcoma cell line which contained the kinase domain of the Met gene fused to a dimerization domain at its N-terminus [C. S. Cooper et al., *Nature* 311: 29-33 (1984)].

The cellular Met protein is a heterodimeric transmembrane protein synthesized as a single chain 190 kd precursor [G. A. Rodrigues et al., *Mol. Cell. Biol.* 11: 2962-70 (1991)]. The precursor is cleaved intracellularly after amino acid residue 307 to form the 50 kd α-chain and the 145 kd β-chain, which are connected by disulfide bridges. The α-chain is entirely extracellular, whereas the β-chain spans the plasma membrane. The β-chain is composed of an N-terminal sema domain, which together with the α-chain mediates ligand binding. The remainder of the ectodomain of the β-chain is composed of a cysteine-rich domain and four immunoglobulin domains and is followed by the transmembrane region and the intracellular domain. The intracellular domain contains a juxtamembrane domain, the kinase domain and a C-terminal domain, which mediates the downstream signalling. Upon ligand binding, a dimerization of the receptor is induced, and the kinase domain is activated by a cascade of tyrosine autophosphorylation steps in the juxtamembrane region (Y1003), the activation loop of the kinase (Y1234 and Y1235) and the carboxy-terminal domain (Y1349 and Y1356). Phosphorylated Y1349 and Y1356 comprise the multi-substrate docking site for binding adapter proteins necessary for downstream c-Met signalling [C. Ponzetto et al., *Cell* 77: 261-71 (1994)]. One of the most crucial substrates for c-Met signalling is the scaffolding adaptor protein Gab1, which binds to either Y1349 or Y1356 via an unusual phosphotyrosine binding site (termed mbs: met binding site) which causes a unique prolonged intracellular signal. Another important substrate is the adaptor protein Grb2. Depending on the cellular context, these adaptors mediate the activation of various intracellular signal pathways like the ones signalling via ERK/MAPK, PI3K/Akt, Ras, JNK, STAT, NFκB and β-catenin.

c-Met is uniquely activated by hepatocyte growth factor (HGF), also known as scatter factor, and its splice variants, which is its only known biologically active ligand [L. Naldini et al., *Oncogene* 6: 501-4 (1991)]. HGF has a distinct structure which reveals similarities to proteinases of the plasminogen family. It is composed of an amino-terminal domain followed by four kringle domains and a serine protease homology domain, which is not enzymatically active. Similar to c-Met, HGF is synthesized as an inactive single chain precursor (pro-HGF), which is extracellularly cleaved by serine proteases (e.g. plasminogen activators and coagulation factors) and converted into a disulfide-linked active α- and β-chain heterodimer. HGF binds heparan sulfate proteoglycans with high affinity, which keeps it mainly associated with the extracellular matrix and limits its diffusion. Crystal structure analyses indicate that HGF forms a dimer, which upon binding to c-Met induces dimerization of the receptor.

HGF is expressed by mesenchymal cells, and its binding to c-Met, which is widely expressed in particular in epithelial cells, results in pleiotropic effects in a variety of tissues including epithelial, endothelial, neuronal and hematopoetic cells. The effects generally include one or all of the following phenomena: i) stimulation of mitogenesis; HGF was identified by its mitogenic activity on hepatocytes; ii) stimulation of invasion and migration; in an independent experimental approach, HGF was identified as scatter factor based on its induction of cell motility ("scattering"); and iii) stimulation of morphogenesis (tubulogenesis). HGF induces the formation of branched tubules from canine kidney cells in a collagen matrix. Furthermore, evidence from genetically modified mice and from cell culture experiments indicate that c-Met acts as a survival receptor and protects cells from apoptosis [N. Tomita et al., *Circulation* 107: 1411-1417 (2003); S. Ding et al., *Blood* 101: 4816-4822 (2003); Q. Zeng et al., *J. Biol. Chem.* 277: 25203-25208 (2002); N. Horiguchi et al., *Oncogene* 21: 1791-1799 (2002); A. Bardelli et al., *Embo J.* 15: 6205-6212 (1996); P. Longati et al., *Cell Death Differ.* 3: 23-28 (1996); E. M. Rosen, *Symp. Soc. Exp. Biol.* 47: 227-234 (1993)]. The coordinated execution of these biological processes by HGF results in a specific genetic program which is termed as "invasive growth".

Under normal conditions, c-Met and HGF are essential for embryonic development in mice, in particular for the development of the placenta and the liver and for the directional migration of myoblasts from the somites of the limbs. Genetic disruption of the c-Met or HGF genes results in identical phenotypes which shows their unique interaction. The physiological role of c-Met/HGF in the adult organism is less well understood, but experimental evidence suggests that they are involved in wound healing, tissue regeneration, hemopoiesis and tissue homeostasis.

The identification of the oncoprotein TPR-MET was a first hint that c-Met may play a role in tumourigenesis. Additional substantial evidence is derived from a number of different experimental approaches. Overexpression of c-Met or HGF in human and murine cell lines induces tumouri-genicity and a metastatic phenotype when expressed in nude mice. Transgenic overexpression of c-Met or HGF induces tumourigenesis in mice.

Most intriguingly, missense mutations of c-Met or mutations which activate the receptor have been identified in sporadic and hereditary papillary kidney carcinomas (HPRC) as well as in other cancer types like lung, gastric, liver, head and neck, ovarian and brain cancers. Significantly, specific c-Met mutations in HPRC families segregate with disease, forming a causal link between c-Met activation and human cancer [L. Schmidt et al., *Nat. Genet.* 16: 68-73 (1997); B. Zbar et al., *Adv. Cancer Res.* 75: 163-201 (1998)]. Activation mutations with the strongest transforming activities are located in the activation loop (D1228N/H and Y1230H/D/C) and in the adjacent P+1 loop (M1250T). Additional weaker mutations have been found near the catalytic loop and within the A lobe of the kinase domain. Furthermore, some mutations in the juxtamembrane domain of c-Met have been observed in lung tumours which do not directly activate the kinase, but rather stabilize the protein by rendering it resistant to ubiquitination and subsequent degradation [M. Kong-Beltran et al., *Cancer Res.* 66: 283-9 (2006); T. E. Taher et al., *J. Immunol.* 169: 3793-800 (2002); P. Peschard et al., *Mol. Cell* 8: 995-1004 (2001)]. Interestingly, somatic mutations of c-Met are associated with increased aggressiveness and extensive metastases in various cancers. While the frequency of germ line and somatic mutations is low (below 5%), other major mechanisms have been observed leading to a deregulation of the c-Met signalling, in the absence of mutations, by paracrine or autocrine mechanisms. Paracrine activation has been observed in tumours which are derived from mesenchymal cells, like osteosarcomas or rhabdomyosarcomas, which physiologically produce HGF, and in glioblastomas and mamma carcinomas which are of ectodermal origin.

However, the most frequent cases are carcinomas where c-Met is overexpressed as observed in carcinomas of the colon, pancreas, stomach, breast, prostate, ovary and liver. Overexpression may arise, for example, by gene amplification as observed in gastric and lung tumour cell lines. Very recently, overexpression of c-Met was detected in lung tumour cell lines which acquired resistance to EGF receptor inhibition [J. A. Engelmann et al., *Science* 316: 1039-1043 (2007)]. Some epithelial tumours that overexpress c-Met also co-express HGF, resulting in an autocrine c-Met/HGF stimulatory loop and thereby circumventing the need for stromal cell-derived HGF.

In general, it has been found that aberrant activation of c-Met in human cancer is typically associated with a poor prognosis, regardless of the specific mechanism [J. G. Christensen et al., *Cancer Lett.* 225: 1-26 (2005)].

In summary, a great number of in vitro and in vivo studies have been performed that validate c-Met as an important cancer target, and a comprehensive list can be viewed at http://www.vai.org/met [C. Birchmeier et al., *Nat. Rev. Mol. Cell Biol.* 4: 915-25 (2003)]. Several strategies have been followed to attenuate aberrant Met signalling in human tumours including HGF antagonists and small molecule inhibitors, amongst others. A number of small molecule inhibitors are currently in clinical development, such as ARQ-197 (Arqule), foretinib (XL-880, Exelixis/GSK), and PH-2341066 (Pfizer); they have recently been reviewed [J. J. Cui, *Expert Opin. Ther. Patents* 17: 1035-45 (2007)].

In WO 2006/066011-A2, haloalkyl-substituted 3-cyano-1, 4-dihydropyridine derivatives with an aryl or heteroaryl group in 4-position have been described as modulators both of steroidal receptors and calcium channel activities thus being especially useful for the treatment of cardiovascular diseases. A method for the treatment of Alzheimer's disease using 4-phenyl-1,4-dihydropyridine derivatives has been claimed in WO 2006/074419-A2.

Variously substituted 3-cyano-4-heteroaryl-1,4-dihydropyridines possessing c-Met kinase inhibitory activity have recently been disclosed in WO 2008/071451-A1. During further investigation of this novel structural class of c-Met inhibitors it emerged, however, that candidate compounds were frequently compromised by an unsatisfactory oral bioavailability which turned out to be significantly lower than initially expected from blood clearance determinations in rats. As oral bioavailability also depends on how well a compound is absorbed, and given the pharmacokinetic and physico-chemical profile of these compounds, it was hypothesized that low solubility and/or inadequate permeability across the gastro-intestinal tract might lead to such limitations in the absorption.

The technical problem to be solved according to the present invention may therefore be seen in identifying alternative compounds with potent inhibitory activity on the c-Met kinase which would reveal an increase in solubility and/or permeability, subsequently leading to an increase of the fraction absorbed after peroral administration of these compounds.

Surprisingly, it has now been found that certain 3,5-dicyano-4-(1H-indazol-5-yl)-2,6-dimethyl-1,4-dihydropyridine derivatives in which at least one of the methyl groups in position 2 and 6 is replaced by a difluoromethyl or a substituted difluoromethyl group exhibit significantly improved permeability properties in vitro which also translate into an increased oral bioavailability of such compounds as confirmed by pharmacokinetic in vivo studies in rats.

Thus, in one aspect, the present invention relates to fluoro-substituted 3,5-dicyano-4-(1H-indazol-5-yl)-2,6-dimethyl-1,4-dihydropyridine derivatives of the general formula (1)

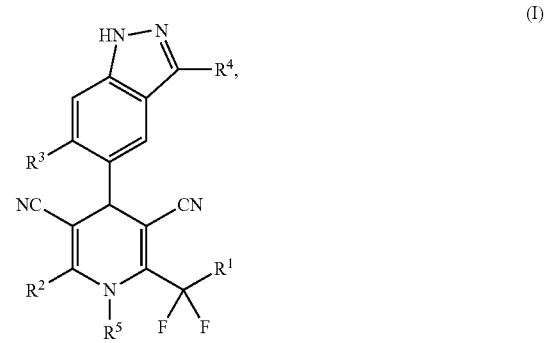

wherein
$R^1$ is hydrogen, fluoro, methyl or ethyl,
$R^2$ is methyl, difluoromethyl or trifluoromethyl,
$R^3$ is hydrogen or fluoro,
$R^4$ is hydrogen, methyl or ethyl,
and
$R^5$ is hydrogen or methyl.

In a preferred embodiment, the present invention relates to compounds of formula (I), wherein
$R^5$ is hydrogen.

In another preferred embodiment, the present invention relates to compounds of formula (I), wherein
$R^1$ is hydrogen or fluoro.

In a further preferred embodiment, the present invention relates to compounds of formula (I), wherein $R^1$ is hydrogen or fluoro,
$R^2$ is methyl or difluoromethyl,
$R^3$ is hydrogen or fluoro,
$R^4$ is hydrogen or methyl,
and
$R^5$ is hydrogen.

In a particularly preferred embodiment, the present invention relates to compounds according to formula (I) selected from the group consisting of the following compounds rac-2-Methyl-4-(3-methyl-1H-indazol-5-yl)-6-(trifluoromethyl)-1,4-dihydropyridine-3,5-dicarbonitrile;
(4R)-2-Methyl-4-(3-methyl-1H-indazol-5-yl)-6-(trifluoromethyl)-1,4-dihydropyridine-3,5-dicarbonitrile;
(4S)-2-Methyl-4-(3-methyl-1H-indazol-5-yl)-6-(trifluoromethyl)-1,4-dihydropyridine-3,5-dicarbonitrile;
rac-2-(Difluoromethyl)-4-(6-fluoro-3-methyl-1H-indazol-5-yl)-6-methyl-1,4-dihydropyridine-3,5-dicarbonitrile;
(4R)-2-(Difluoromethyl)-4-(6-fluoro-3-methyl-1H-indazol-5-yl)-6-methyl-1,4-dihydropyridine-3,5-dicarbonitrile;
(4S)-2-(Difluoromethyl)-4-(6-fluoro-3-methyl-1H-indazol-5-yl)-6-methyl-1,4-dihydropyridine-3,5-dicarbonitrile;
2,6-Bis(difluoromethyl)-4-(3-methyl-1H-indazol-5-yl)-1,4-dihydropyridine-3,5-dicarbonitrile;
2,6-Bis(difluoromethyl)-4-(6-fluoro-3-methyl-1H-indazol-5-yl)-1,4-dihydropyridine-3,5-dicarbonitrile;
and
rac-4-(6-Fluoro-1H-indazol-5-yl)-2-methyl-6-(trifluoromethyl)-1,4-dihydropyridine-3,5-dicarbonitrile.

Furthermore, it was unexpectedly found that compounds of the present invention containing an unsubstituted dihydropyridine nitrogen atom [$R^5$ in formula (I)=H] can be converted into stable salt forms under moderately basic conditions, yielding well-defined 1,4-dihydropyridinides with a deprotonated nitrogen atom. These unprecedented findings provide an additional option to increase solubility and to beneficially influence absorption properties.

Thus, in a second aspect, the present invention relates to salts of fluoro-substituted 3,5-dicyano-4-(1H-indazol-5-yl)-2,6-dimethyl-1,4-dihydropyridines with the general formula (I-A)

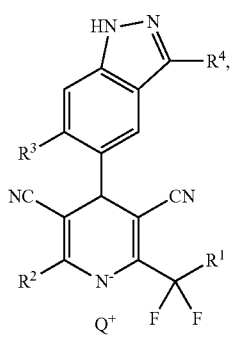

(I-A)

wherein
$R^1$, $R^2$, $R^3$ and $R^4$ have the meanings indicated above,
and
$Q^+$ is an alkali metal cation or a quaternary ammonium cation.

In a preferred embodiment, the present invention relates to dihydropyridine salts of formula (I-A), wherein
$Q^+$ is a sodium or potassium cation or a 2-hydroxyethyltrimethyl ammonium (choline) cation.

In a particularly preferred embodiment, the present invention relates to dihydropyridine salts of formula (I-A), wherein
$Q^+$ is a 2-hydroxyethyltrimethyl ammonium (choline) cation.

The compounds and salts according to this invention can also be present in the form of hydrates or solvates.

Salts for the purposes of the present invention are preferably pharmaceutically acceptable salts of the compounds according to the invention (for example, see S. M. Berge et al., "Pharmaceutical Salts", J. Pharm. Sci. 1977, 66, 1-19).

Hydrates of the compounds or salts of the invention are stoichiometric compositions of the compounds or salts with water, such as, for example, hemi-, mono- or dihydrates.

Solvates of the compounds or salts of the invention are stoichiometric compositions of the compounds or salts with solvents.

A quaternary ammonium cation in the context of the present invention refers to a tetraalkyl ammonium cation having four identical or different, straight-chain or branched alkyl groups attached to the nitrogen atom, wherein each alkyl group has 1 to 6 carbon atoms, and wherein each alkyl group may be further substituted with a hydroxy group. Examples which may be preferably mentioned are: tetramethyl ammonium, tetraethyl ammonium, tetra-n-butyl ammonium, and 2-hydroxyethyltrimethyl ammonium (choline).

The compounds and salts of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

All isomers, whether separated, pure, partially pure, or in diastereomeric or racemic mixture, of the compounds of this invention are encompassed within the scope of this invention. It will be appreciated that pure diastereomers and pure enantiomers represent preferred embodiments. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds and salts described above are included according to the present invention.

In another embodiment, the present invention relates to a process for preparing the compounds of general formula (I) and/or the dihydropyridine salts of general formula (I-A), characterized in that an indazolyl aldehyde of formula (II)

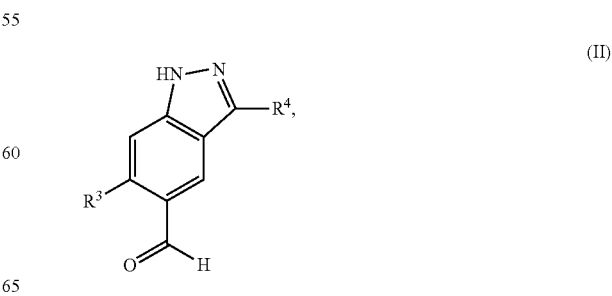

(II)

wherein $R^3$ and $R^4$ have the meanings described above, is first reacted with a ketonitrile of formula (III)

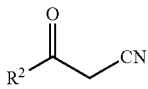 (III)

or a sodium enolate thereof, wherein $R^2$ has the meaning described above,
in the presence of an acid, acid/base combination and/or dehydrating agent to give a compound of formula (IV)

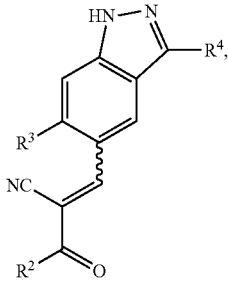 (IV)

wherein $R^2$, $R^3$ and $R^4$ have the meanings described above,
and the latter is then condensed either with an enaminonitrile of formula (V)

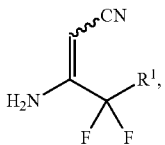 (V)

wherein $R^1$ has the meaning described above,
or with a ketonitrile of formula (VI)

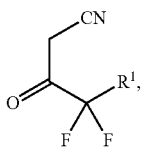 (VI)

wherein $R^1$ has the meaning described above,
in the presence of an ammonia source such as ammonium acetate to give the compound of formula (I-B)

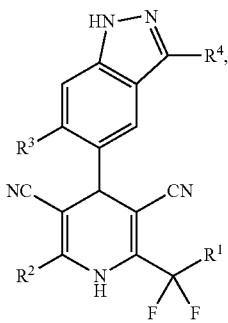 (I-B)

wherein $R^1$, $R^2$, $R^3$ and $R^4$ have the meanings described above, optionally followed by
[A] dihydropyridine N-methylation employing a compound of formula (VII)

$$CH_3—X \quad (VII),$$

wherein
X represents a leaving group such as halogen, mesylate, triflate, tosylate or sulfate, in the presence of a base to give the compound of formula (I-C)

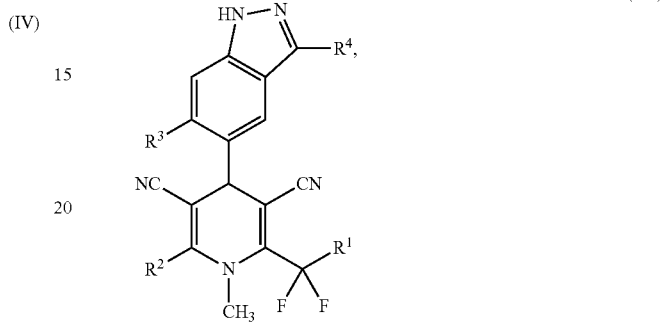 (I-C)

wherein $R^1$, $R^2$, $R^3$ and $R^4$ have the meanings described above,
or
[B] dihydropyridine salt formation by treatment with an agent of formula (VIII)

$$Q^+Z^- \quad (VIII),$$

wherein $Q^+$ has the meaning described above,
and
$Z^-$ represents a basic anion such as hydroxide, carbonate or bicarbonate,
to yield the 1,4-dihydropyridinide salt of formula (I-A)

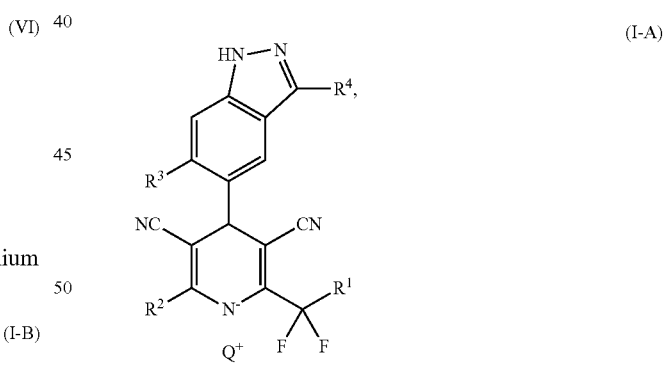 (I-A)

wherein $R^1$, $R^2$, $R^3$, $R^4$ and $Q^+$ have the meanings described above,
and optionally followed, where appropriate, by (i) separating the compounds (I-B) and (I-C) into their respective enantiomers, preferably using chromatographic methods, and/or (ii) converting the compounds (I-B) and (I-C) or the salts (I-A) into their respective hydrates or solvates by treatment with the corresponding solvents.

The process sequence (II)+(III)→(IV), (IV)+(V)→(I-B) may be carried out in two separate steps as described above, or by using a one-pot procedure, i.e. without explicit isolation of intermediate compound (IV); in some cases, depending on the reactivity of individual reactants, it may also be feasible to perform a one-flask/three-component condensation reaction of compounds (II), (III) and (V) [for the synthesis of 1,4-dihydropyridines in general, see, for example, D. M. Stout, A. I. Meyers, *Chem. Rev.* 1982, 82, 223-243; H. Meier et al., *Liebigs Ann. Chem.* 1977, 1888; H. Meier et al., ibid. 1977, 1895; H. Meier et al., ibid. 1976, 1762; F. Bossert et al., *Angew. Chem.* 1981, 93, 755].

Process steps (II)+(III)→(IV) and (IV)+(V)/(VI)→(I-B) are generally carried out in an inert solvent at a temperature ranging from +20° C. to the boiling point of the solvent under atmospheric pressure.

Solvents suitable for this purpose are, for example, alcohols such as methanol, ethanol, n-propanol, isopropanol, n-butanol, tert-butanol or n-pentanol, hydrocarbons such as hexane, cyclohexane, benzene, toluene or xylene, halohydrocarbons such as dichloromethane, trichloromethane, tetrachloromethane, trichloroethane, 1,2-dichloroethane, chlorobenzene or chlorotoluene, ethers such as tetrahydrofuran, 1,4-dioxane or 1,2-dimethoxyethane, or other solvents such as acetonitrile or acetic acid. It is also feasible to use mixtures of these solvents. Reaction (II)+(III)→(IV) is preferably performed in dichloromethane, toluene, ethanol, n-propanol, isopropanol, n-butanol or n-pentanol at the respective reflux temperature under atmospheric pressure, and reaction (IV)+(V)/(VI)→(I-B) is preferably carried out in ethanol, n-propanol, isopropanol, n-butanol, n-pentanol, xylene or acetic acid also at reflux temperature under atmospheric pressure.

Reaction (II)+(III)→(IV) may advantageously take place in the presence of an acid or acid/base combination and optionally a dehydrating agent such as, for example, molecular sieves. Examples of suitable acid catalysts are acetic acid, trifluoroacetic acid, methanesulfonic acid or p-toluenesulfonic acid; suitable bases are in particular piperidine or pyridine. Depending on the reactivity of the components, conversion (IV)+(V)→(I-B) may be performed without further auxiliary reagents, or it can be facilitated either by an acid, such as acetic acid, or by a tertiary amine base, such as triethylamine or pyridine. Reaction (IV)+(VI)→(I-B) is usually carried out in the presence of an acid; preferably, acetic acid is used both as acid catalyst and solvent or co-solvent.

Suitable ammonia sources for reaction (IV)+(VI)→(I-B) are, for example, ammonium formate, ammonium acetate, ammonium chloride or ammonium hydrogensulfate; preference is given to ammonium acetate.

Inert solvents for the methylation reaction (I-B)+(VII)→(I-C) are, for example, ethers such as diethyl ether, methyl tert-butyl ether, tetrahydrofuran, 1,4-dioxane or 1,2-dimethoxyethane, hydrocarbons such as benzene, toluene, xylene, hexane or cyclohexane, halohydrocarbons such as dichloromethane, trichloromethane, tetrachloromethane, 1,2-dichloroethane, trichloroethane, tetra-chloroethane, chlorobenzene or chlorotoluene, or other solvents such as acetonitrile, N,N-dimethylformamide (DMF), dimethylsulfoxide (DMSO), N,N'-dimethylpropylene urea (DMPU), N-methyl-pyrrolidinone (NMP) or pyridine. It is also feasible to use mixtures of these solvents. Preferably, dichloromethane, tetrahydrofuran, N,N-dimethylformamide or mixtures thereof are employed.

Bases suitable for process step (I-B)+(VII)→(I-C) are in particular alkali metal or alkaline earth metal carbonates such as lithium, sodium, potassium, calcium or caesium carbonate, alkali metal hydrides such as sodium or potassium hydride, sterically hindered alkali alkoxides such as sodium or potassium tert-butoxide, sterically hindered alkali amides such as lithium, sodium or potassium bis(trimethylsilyl)amide or lithium diisopropylamide, or organic amines such as triethylamine, N-methylmorpholine, N-methylpiperidine, N,N-diisopropylethylamine or pyridine. Potassium carbonate, caesium carbonate or sodium hydride are preferably used.

Reaction (I-B)+(VII)→(I-C) is generally performed under atmospheric pressure at a temperature range from −20° C. to +100° C., preferably at 0° C. to +50° C.

In the salt forming reaction (I-B)+(VIII)→(I-A), the agent (VIII) is usually employed as an aqueous solution, and the conversion is preferably carried out in a water-miscible solvent, such as ethanol or tetrahydrofuran, at a temperature ranging from +20° C. to the boiling point of the solvent under atmospheric pressure.

Compounds of formula (I), wherein $R^1$ is hydrogen and $R^2$ is difluoromethyl, or wherein $R^1$ is fluoro and $R^2$ is trifluoromethyl [i.e. compounds of formula (I) with a symmetrical dihydropyridine 2,6-disubstitution], and the corresponding salts of formula (I-A) can alternatively be prepared by condensing the indazolyl aldehyde of formula (II)

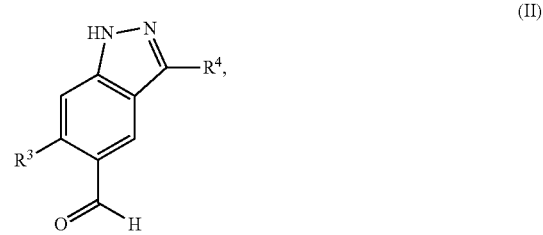

(II)

wherein $R^3$ and $R^4$ have the meanings described above, with two equivalents of an enaminonitrile of formula (V-A)

(V-A)

wherein $R^{14}$ represents hydrogen or fluoro, in the presence of an acid and optionally a dehydrating agent to give the compound of formula (I-D)

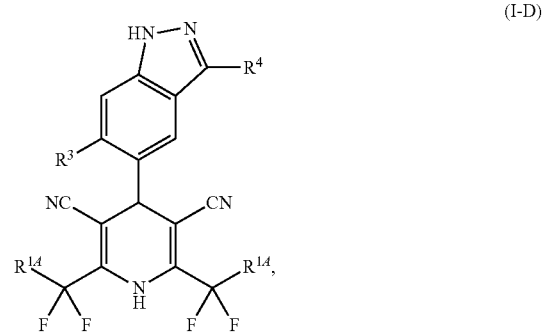

(I-D)

wherein $R^{14}$, $R^3$ and $R^4$ have the meanings described above, which may then be converted into the N-methylated derivative of formula (I-E)

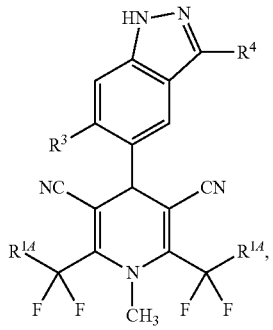

(I-E)

wherein $R^{14}$, $R^3$ and $R^4$ have the meanings described above, or the 1,4-dihydropyridinide salt of formula (I-F)

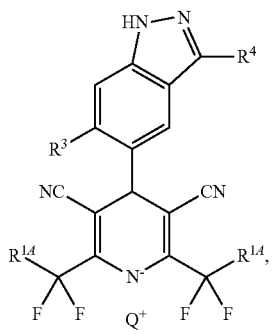

(I-F)

wherein $R^{14}$, $R^3$, $R^4$ and $Q^+$ have the meanings described above, in analogy to the transformations [A] and [B], respectively, as described above.

Process step (II)+(V-A)→(I-D) is usually performed in protic organic solvents like alcohols, such as methanol, ethanol, n-propanol, isopropanol, n-butanol, tert-butanol or n-pentanol, or like acetic acid. It is also possible to use mixtures of these solvents. Advantageously, the reaction is run in the presence of an acid catalyst, such as acetic acid, trifluoroacetic acid, methanesulfonic acid or p-toluenesulfonic acid, optionally with a dehydrating agent, such as molecular sieves, as further additive. Preferably, acetic acid is simultaneously used as solvent and acid catalyst.

Reaction (II)+(V-A)→(I-D) is generally carried out at a temperature ranging from +20° C. to the boiling point of the respective solvent under atmospheric pressure, preferably at a range from +60° C. to +120° C.

For transformations (I-D)→(I-E) and (I-D)→(I-F), similar reaction conditions, such as solvents, bases and temperatures, apply as described above for the analogous conversions (I-B)→(I-C) and (I-B)→(I-A), respectively.

The compounds of the formulae (II), (III), (V), (V-A), (VI), (VII) and (VIII) are either commercially available, known from the literature, or can be prepared from readily available starting materials by adaptation of standard methods described in the literature (for further references, see experimental section below).

The preparation of the compounds of the invention can be illustrated by means of the following synthesis schemes. More detailed procedures are presented below in the experimental section describing the Examples.

Scheme 1

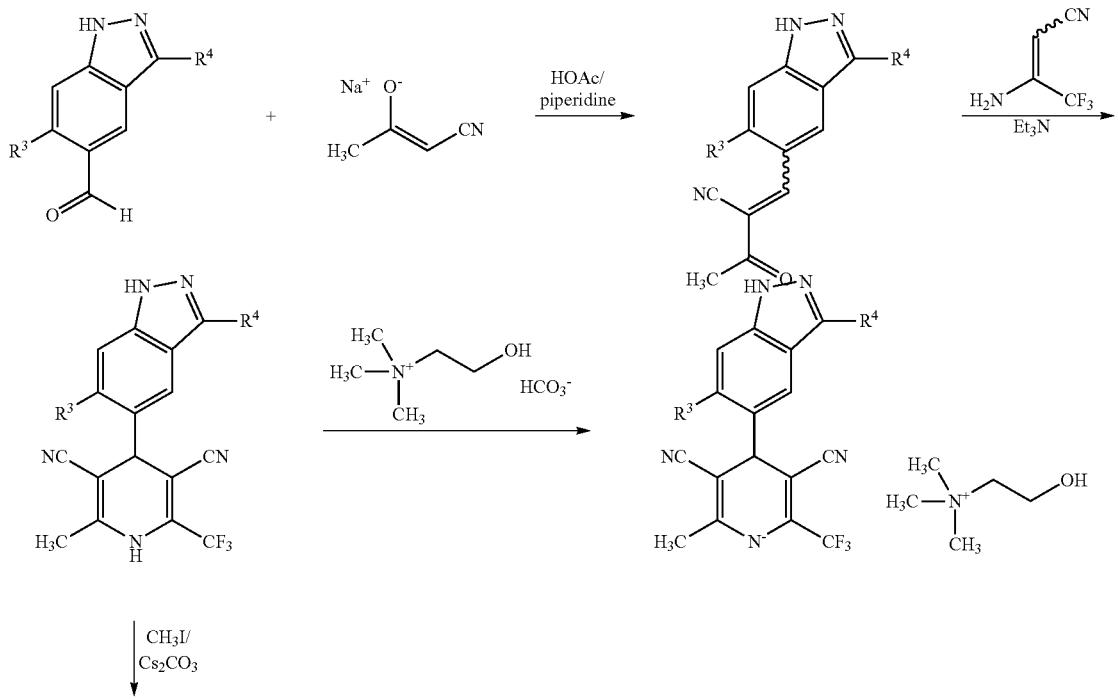

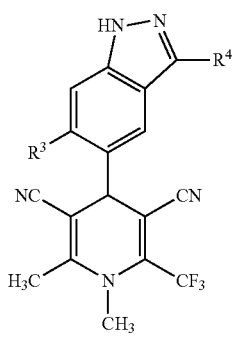

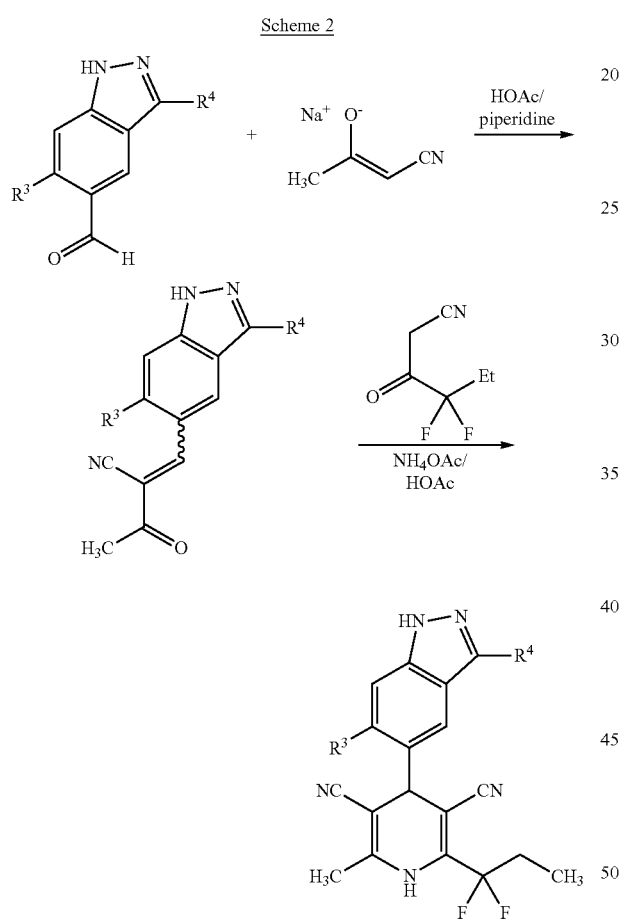

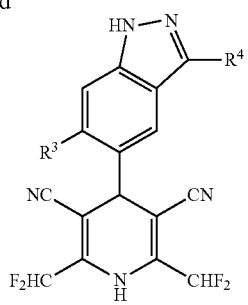

In the following, for the sake of brevity, the expressions "compounds of the invention", "compounds of formula (I)" and the like are generally meant to also include the dihydropyridine salts of formula (I-A) derived therefrom.

Methods of Use

The compounds of the present invention are potent inhibitors of the activity or expression of receptor tyrosine kinases, particularly of the c-Met receptor tyrosine kinase. Moreover, the compounds of the invention are characterized by a high permeability in intestinal epithelial cells, resulting in a significantly improved bioavailability (i.e. increased fraction absorbed) of these compounds after peroral administration. Therefore, the compounds of formula (I) are expected to be highly valuable as therapeutic agents.

Accordingly, in another embodiment, the present invention provides a method of treating disorders relating to or mediated by c-Met kinase activity in a patient in need of such treatment, comprising administering to the patient an effective amount of a compound of formula (I) as defined above. In certain embodiments, the disorders relating to c-Met kinase activity are cell proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

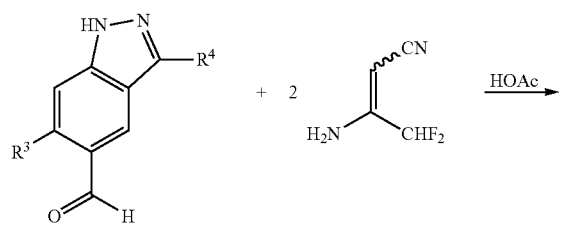

The term "disorders relating to or mediated by c-Met" shall include diseases associated with or implicating c-Met activity, for example the hyperactivity of c-Met, and conditions that accompany with these diseases. Examples of "disorders relating to or mediated by c-Met" include disorders resulting from overstimulation of c-Met due to abnormally high amount of c-Met or mutations in c-Met, or disorders resulting from abnormally high amount of c-Met activity due to abnormally high amount of c-Met or mutations in c-Met.

The term "hyperactivity of c-Met" refers to either c-Met expression in cells which normally do not express c-Met or c-Met activity by cells which normally do not possess active c-Met or increased c-Met expression leading to unwanted cell proliferation or mutations leading to constitutive activation of c-Met.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, skeletal disorders, angiogenic or blood vessel proliferative disorders, pulmonary hypertension, fibrotic disorders, mesangial cell proliferative disorders, colonic polyps, polycystic kidney disease, benign prostate hyper-plasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuro-ectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, athero-sclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with sub-epidermal blister formation, including bullous pemphigoid, erythema multiforme and dermatitis herpetiformis.

The compounds of the present invention may also be used to prevent and treat diseases of the airways and the lung, diseases of the gastro-intestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxo-rubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L 19-IL2 and other IL2 derivatives, filgrastim, lentinan, sizofilan, TheraCys, ubenimex, aldesleukin, alemtuzumab, BAM-002, dacarbazine, daclizumab, deni-leukin, gemtuzumab, ozogamicin, ibritumomab, imiquimod, lenograstim, lentinan, melanoma vaccine (Corixa), molgramostim, sargramostim, tasonermin, tecleukin, thymalasin, tositu-momab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, bevacizumab, brivanib alaninat, cilengtide, combretastatin, endostatin, fenretinide, halofuginone, pazopanib, ranibizumab, rebimastat, recentin, regorafenib, removab, revlimid, sorafenib, squalamine, sunitinib, telatinib, thalidomide, ukrain, vatalanib, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, regorafenib, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, regorafenib, bosutinib, sorafenib, bevacizumab, sunitinib, cediranib, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors (for example, EGFR inhibitors), mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

Abbreviations and Acronyms

Ac acetyl
aq. aqueous (solution)
br. s broad singlet (NMR)
cat. catalytic
conc. concentrated
ΔH melting (or decomposition) enthalpy
d doublet (NMR)
DCI direct chemical ionization (MS)
dd doublet of doublets (NMR)
DMF N,N-dimethylformamide
DMSO dimethylsulfoxide
DMSO-$d_6$ dimethylsulfoxide-$d_6$
DSC differential scanning calorimetry
ee enantiomeric excess
EI electron impact ionization (MS)
equiv. equivalent(s)
ESI electro-spray ionization (MS)
Et ethyl
FT-IR Fourier transform infrared spectrometry
GC-MS gas chromatography-coupled mass spectrometry
h hour(s)
$^1$H-NMR proton nuclear magnetic resonance spectrometry
HOAc acetic acid
HPLC high performance/high pressure liquid chromatography
LC-MS liquid chromatography-coupled mass spectrometry
m multiplet (NMR)
Me methyl
min minute(s)
MS mass spectrometry
m/z mass-to-charge ratio
NMP N-methylpyrrolidin-2-one
of th. of theory (chemical yield)
q quartet (NMR)
rac racemic, racemate
$R_f$ TLC retention factor
RP reverse phase (HPLC)
rt room temperature
$R_t$ retention time (HPLC)
s singlet (NMR)
sept septet (NMR)
TBAF tetra-n-butylammonium fluoride
tBu tert-butyl
TFA trifluoroacetic acid
THF tetrahydrofuran
TLC thin layer chromatography
t triplet (NMR)
v/v volume-to-volume ratio
w/v weight-to-volume ratio
w/w weight-to-weight ratio LC-MS and GC-MS Methods:

Method 1 (LC-MS):

Instrument: Micromass ZQ with HPLC Waters Alliance 2795; column: Phenomenex Synergi 2.5μ MAX-RP 100A Mercury, 20 mm×4 min; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.

Method 2 (LC-MS):

Instrument: Micromass Quattro Premier with HPLC Waters HPLC Acquity; column: Thermo Hypersil GOLD 1.9μ, 50 mm×1 mm; eluent A: 1 L water+0.5 mL 50% formic acid, eluent B: 1 L acetonitrile+0.5 mL 50% formic acid; gradient: 0.0 min 90% A→0.1 min 90% A→1.5 min 10% A→2.2 min 10% A; oven: 50° C.; flow rate: 0.33 mL/min; UV detection: 210 nm.

Method 3 (LC-MS):

Instrument: Micromass Quattro Micro with HPLC Agilent 1100 Series; column: Thermo Hypersil GOLD 3μ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.01 min 100% A (flow rate 2.5 mL/min)→5.00 min 100% A; oven: 50° C.; flow rate: 2 mL/min; UV detection: 210 nm.

Method 4 (LC-MS):

Instrument: Waters Acquity SQD HPLC System; column: Waters Acquity HPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm.

Method 5 (GC-MS):

Instrument: Micromass GCT, GC 6890; column: Restek RTX-35, 15 m×200 μm×0.33 μm; constant flow with helium:

0.88 mL/min; oven: 70° C.; inlet: 250° C.; gradient: 70° C., 30° C./min→310° C. (keep for 3 min).

Starting Materials and Intermediates

Example 1A

3-Methyl-1H-indazole-5-carbaldehyde

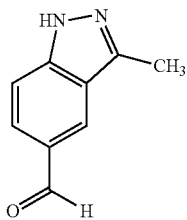

Tetrahydrofuran (600 ml) was cooled down to −78° C. under argon atmosphere. At this temperature, a 1.7 M solution of tert-butyllithium in n-pentane (200 ml) was added dropwise. After 15 minutes at −78° C., a solution of 22.4 g (106.1 mmol) 5-bromo-3-methyl-1H-indazole in THF (300 ml) was added dropwise at such a rate that the temperature of the solution did not exceed −70° C. The mixture was stirred for 30 minutes before N,N-dimethylformamide (24.5 ml) was added dropwise. After 20 min, the cooling bath was removed, and stirring was continued for 1 h before water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 18.5 g of crude 3-methyl-1H-indazole-5-carbaldehyde, which was used in the next step without further purification.

$^1$H-NMR (DMSO-d$_6$): δ=13.13 (br. s, 1H), 10.01 (s, 1H), 8.40 (s, 1H), 7.81 (d, 1H), 7.58 (d, 1H), 2.56 (s, 3H) ppm.

Example 2A (2E)-2-[(3-Methyl-1H-indazol-5-yl)methylidene]-3-oxobutanenitrile

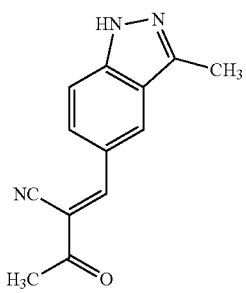 [SMILES: CC(=O)/C(C#N)=C/c1ccc2[nH]nc(C)c2c1]

A mixture of 5.0 g (31.2 mmol) 3-methyl-1H-indazole-5-carbaldehyde (Example 1A), 3.61 g (34.3 mmol) sodium (1Z)-1-cyanoprop-1-en-2-olate, 2.23 ml (39 mmol) acetic acid and 0.31 ml (3.12 mmol) piperidine in dry dichloromethane (250 ml) containing 4 Å molecular sieve was stirred under reflux for 12 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (3.5 g, 50% of th.) as a pale yellow solid which was used in the next step without further purification.

LC-MS (method 1): R$_t$=1.32 min; MS (ESIpos): m/z=226 (M+H)$^+$ $^1$H-NMR (400 MHz, DMSO-d$_6$): δ=13.18 (br. s, 1H), 8.52 (s, 1H), 8.49 (s, 1H), 8.19 (d, 1H), 7.69 (d, 1H), 2.55 (br. m, 6H) ppm.

Example 3A

6-Fluoro-3-methyl-1H-indazole-5-carbaldehyde

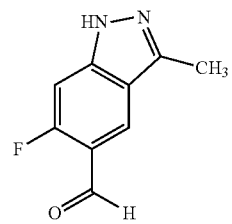

A solution of 30 g (131 mmol) 5-bromo-6-fluoro-3-methyl-1H-indazole [preparation described in WO 2005/085227-A1, Example 104c); also commercially available, CAS Reg.-No. 864773-66-0] in THF (525 ml) was cooled to −45° C. A solution of methylmagnesium chloride in THF (3 M; 50.2 ml, 151 mmol) was added dropwise at −45° C., and the resulting solution was stirred for 40 min at this temperature. Using a dosing pump, 253 ml (354 mmol) of 2-butyl-lithium solution (1.4 M in cyclohexane) were added so that the temperature did not exceed −40° C. The resulting mixture was stirred for 30 min at −40° C., and then 30.2 ml (393 mmol) N,N-dimethylformamide were added dropwise keeping the temperature at −40° C. The resulting mixture was stirred for 30 min at −40° C., then allowed to warm up to room temperature, and slowly poured into a volume of 2.8 L of 2 N hydrochloric acid cooled to 5° C. (ice-water bath). The mixture was extracted several times with ethyl acetate. The combined organic layers were washed with brine, dried over sodium sulfate, filtered, and concentrated under reduced pressure. The residue was dissolved in dichloromethane and purified by chromatography on silica gel (eluent: pentane/ethyl acetate 6:4 v/v) to afford 19.6 g (78% of th.) of the title compound as a pale yellow solid.

MS (ESIpos): m/z=179 (M+H)$^+$ $^1$H-NMR (400 MHz, DMSO-$d_6$): δ=13.14 (s, 1H), 10.17 (s, 1H), 8.33 (d, 1H), 7.37 (d, 1H), 2.54 (s, 3H) ppm.

Example 4A (2E)-2-[(6-Fluoro-3-methyl-1H-indazol-5-yl)methylidene]-3-oxobutanenitrile

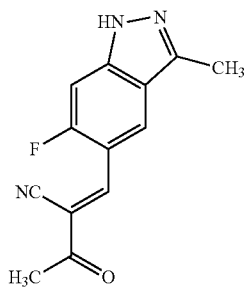 [SMILES: CC(=O)/C(C#N)=C/c1cc2c(C)n[nH]c2cc1F]

Following the procedure described for Example 2A, the title compound was prepared using 2.74 g (15.5 mmol) 6-fluoro-3-methyl-1H-indazole-5-carbaldehyde (Example 3A) and 2.6 g (24.8 mmol) sodium (1Z)-1-cyanoprop-1-en-2-olate to yield 1.6 g (42% of th.) of the crude product which was used in the next step without further purification.

LC-MS (method 4): $R_t$=0.83 min; MS (ESIpos): m/z=244 (M+H)$^+$.

Example 5A

6-Fluoro-1H-indazole-5-carbaldehyde

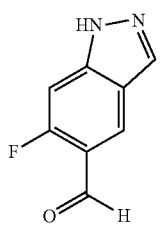

A slurry of 4.8 g (30 mmol) 6-fluoro-1H-indazole-5-carbonitrile [commercially available; preparation given in EP 1 510 516-A1 (production example 82)] in anhydrous toluene (150 ml) was cooled to −40° C. Under inert gas atmosphere, 48 ml (72 mmol) diisobutylaluminium hydride solution (1.5 M in toluene) were added over 30 min, and the resulting mixture was stirred at −40° C. for 3 h. Then, ethyl acetate (30 ml) was added, and the mixture was stirred for further 20 min at −40° C. followed by dropwise addition of aqueous tartaric acid (1 M, 30 ml). The mixture was allowed to warm to 0° C. and filtered at this temperature. The filtrate was extracted with ethyl acetate several times, and the combined organic phases were subsequently washed with saturated aqueous sodium hydrogencarbonate and with brine, dried over sodium sulfate, filtered and concentrated under reduced pressure. The crude product thus obtained (2.60 g, 53% of th.) was used in the next step without further purification.

LC-MS (method 4): $R_t$=0.59 min; MS (ESIpos): m/z=165 (M+H)$^+$.

Example 6A (2E)-2-[(6-Fluoro-1H-indazol-5-yl)methylidene]-3-oxobutanenitrile

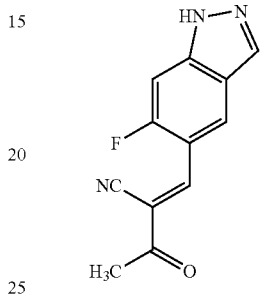

The title compound was prepared from 3.7 g (80% purity, 18.0 mmol) 6-fluoro-1H-indazole-5-carbaldehyde (Example 5A) and 2.08 g (19.84 mmol) sodium (1Z)-1-cyanoprop-1-en-2-olate in analogy to the procedure described in Example 2A yielding 2.5 g (61% of th.) of product which was used in subsequent steps without further purification.

LC-MS (method 2): $R_t$=0.71 min; MS (ESIpos): m/z=230 (M+H)$^+$ $^1$H-NMR (400 MHz, DMSO-$d_6$): δ=13.90 (s, 1H), 8.59 (s, 1H), 8.46 (s, 1H), 8.23 (d, 1H), 7.80 (d, 1H), 2.5 (br. s, 3H) ppm.

Example 7A 1-(5-Bromo-2-fluorophenyl)-1-propanol

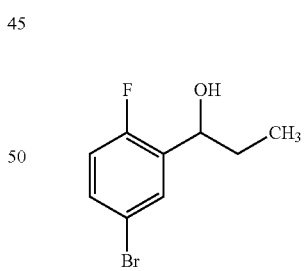

To a solution of 15 g (73.9 mmol) 5-bromo-2-fluorobenzaldehyde in diethyl ether (100 ml) at 0° C. were slowly added 27.1 ml (81.3 mmol) of ethylmagnesium bromide solution (3 M in diethyl ether). After stirring at 0° C. for 3 h, water (20 ml) was carefully added upon which a white precipitate formed. The solid was filtered off and washed with tert-butyl methyl ether. The combined filtrates were washed with brine, dried over sodium sulfate and concentrated under reduced pressure. The crude title compound thus obtained (16.1 g, 93% of th.) was used in the next step without further purification.

GC-MS (method 5): $R_t$=4.54 min; MS (EIpos): m/z=232 (M)⁺.

Example 8A

1-(5-Bromo-2-fluorophenyl)-1-propanone

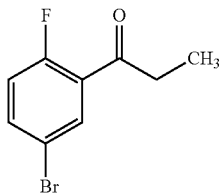

A mixture of 10 g (42.9 mmol) 1-(5-bromo-2-fluorophenyl)-1-propanol (Example 7A), 8.75 g (85.8 mmol) neutral aluminium oxide and 18.5 g (85.8 mmol) pyridinium chlorochromate in dichloromethane (100 ml) was stirred at room temperature for 4 h. The mixture was then filtered through silica gel (0.06-0.2 mm, 200 g) which was washed thoroughly with dichloromethane (1000 ml). The combined filtrates were washed with brine, dried over sodium sulfate and concentrated under reduced pressure. The crude title compound thus obtained (8.6 g, 87% of th.) was used in the next step without further purification.

GC-MS (method 5): $R_t$=4.30 min; MS (EIpos): m/z=230 (M)⁺.

Example 9A

5-Bromo-3-ethyl-1H-indazole

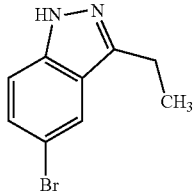

A solution of 7.50 g (32.5 mmol) 1-(5-bromo-2-fluorophenyl)-1-propanone (Example 8A) in 1-methyl-2-pyrrolidinone (NMP; 100 ml) was treated with 3.25 g (3.16 ml, 64.9 mmol) hydrazine hydrate and stirred at reflux temperature for 16 h. Upon cooling, the mixture was poured into a mixture of ice and water. The precipitate was collected by filtration and washed thoroughly with water to yield 4.56 g (62% of th.) of the title compound as a beige-coloured solid.

LC-MS (method 4): $R_t$=1.00 min; MS (ESIpos): m/z=225 (M+H)⁺.

Example 10A

3-Ethyl-1H-indazole-5-carbaldehyde

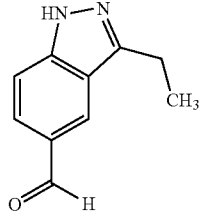

A solution of 6.90 g (30.7 mmol) 5-bromo-3-ethyl-1H-indazole (Example 9A) in THF (300 ml) was cooled to −78° C. At this temperature, 63.1 ml (107 mmol) of tert-butyllithium solution (1.7 M in n-pentane) were slowly added. The mixture was stirred at −78° C. for 30 minutes before N,N-dimethylformamide (80.0 ml) was slowly added. The cooling bath was removed, and stirring was continued until room temperature was reached. Then, water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 4.5 g (84% of th.) of the crude title compound which was used in the next step without further purification.

LC-MS (method 4): $R_t$=0.73 min; MS (ESIpos): m/z=175 (M+H)⁺.

Example 11A

(2E)-2-[(3-Ethyl-1H-indazol-5-yl)methylidene]-3-oxobutanenitrile

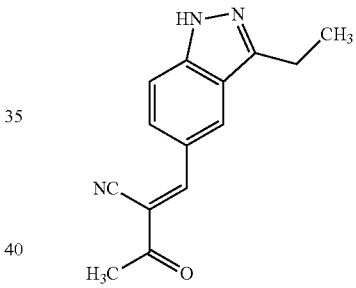

A mixture of 0.50 g (2.87 mmol) 3-ethyl-1H-indazole-5-carbaldehyde (Example 10A), 0.33 g (3.16 mmol) sodium (1Z)-1-cyanoprop-1-en-2-olate, 0.21 ml (3.6 mmol) acetic acid and 0.028 ml (0.29 mmol) piperidine in dry dichloromethane (25 ml) containing 4 Å molecular sieve was stirred under reflux for 16 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (0.60 g, 88% of th.) as a pale yellow solid which was used in subsequent steps without further purification.

LC-MS (method 1): $R_t$=1.50 min; MS (ESIpos): m/z=240 (M+H)⁺

¹H-NMR (400 MHz, DMSO-d₆): δ=13.17 (br. s, 1H), 8.59 (s, 1H), 8.51 (s, 1H), 8.17 (d, 1H), 7.67 (d, 1H), 2.97 (q, 2H), 2.55 (br. m, 3H), 1.36 (t, 3H) ppm.

Example 12A (2E)-2-(1H-Indazol-5-ylmethylidene)-3-oxobutane-nitrile

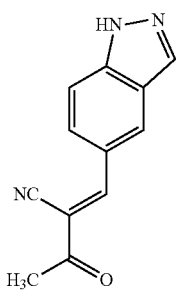 [SMILES: CC(=O)/C(C#N)=C/c1ccc2[nH]ncc2c1]

10 g (68.4 mmol) 1H-indazole-5-carbaldehyde [preparation described in US 2005/0227968-A1 (Intermediate 1)], 7.91 g (75.2 mmol) sodium (1Z)-1-cyanoprop-1-en-2-olate, 4.89 ml (85.5 mmol) acetic acid and 0.68 ml (6.84 mmol) piperidine in dry dichloromethane (500 ml) were stirred at reflux temperature for 7 h using an inverse water separator. Upon cooling, a precipitate was formed which was collected by filtration and washed with dichloromethane. The solid was dried in vacuo to afford the crude title compound (19 g, 75% purity by LC-MS, 96% of th.) which was used in subsequent steps without further purification.

LC-MS (method 2): $R_t$=0.82 min; MS (ESIpos): m/z=212 (M+H)$^+$.

Example 13A 4,4-Difluoro-3-oxohexanenitrile

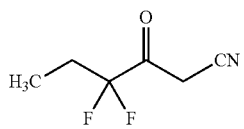

A flame-dried flask was charged with 2.9 ml (4.6 mmol) of n-butyllithium solution (1.6 M in hexanes) in dry THF (14 ml) under inert gas atmosphere and cooled to −78° C. Next, 0.213 ml (4.06 mmol) acetonitrile were slowly added, and the resulting mixture was stirred for 1 h at −70° C. Then, 0.40 g (2.9 mmol) methyl 2,2-difluorobutanoate were slowly added over 5 min maintaining the temperature below −69° C. The reaction mixture was stirred for 2 h at −45° C. and then quenched by addition of 2 N hydrochloric acid (4.8 ml) while keeping the temperature below −20° C. The resulting clear solution was allowed to warm to room temperature and then concentrated under reduced pressure. The crude product thus obtained (2.5 g of 17% purity, 98% of th.) was stored at −21° C. and used in the next step without further purification.

GC-MS (method 5): $R_t$=1.94 min; MS (EIpos): m/z=147 (M)$^+$.

Example 14A 4,4-Difluoro-3-oxobutanenitrile

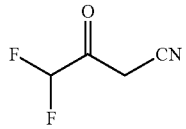

A flame-dried flask was charged with 3.8 ml (6.1 mmol) n-butyllithium solution (1.6 M in hexanes) in dry THF (19 ml) under inert gas atmosphere and cooled to −78° C. Next, 0.28 ml (5.3 mmol) acetonitrile were slowly added, and the resulting mixture was stirred for 1 h at −70° C. Then, 0.4 ml (3.8 mmol) ethyl difluoroacetate were slowly added over 5 min maintaining the temperature below −69° C. The reaction mixture was stirred for 2 h at −45° C. and then quenched by addition of hydrochloric acid (2 M, 4.8 ml) while keeping the temperature below −20° C. The resulting clear solution was allowed to warm to room temperature and then concentrated under reduced pressure. The crude product thus obtained (1.0 g of 46% purity, 99% of th.) was stored at −21° C. and used in the next step without further purification.

GC-MS (method 5): $R_t$=1.49 min; MS (EIpos): m/z=119 (M)$^+$.

Preparation Examples

Example 1 rac-2-(Difluoromethyl)-6-methyl-4-(3-methyl-1H-indazol-5-yl)-1,4-dihydropyridine-3,5-dicarbonitrile

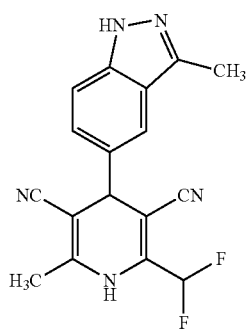 [SMILES: CC1=C(C#N)C(c2ccc3[nH]nc(C)c3c2)C(C#N)=C(C(F)F)N1]

A suspension of 3.42 g (15.2 mmol) (2E)-2-[(3-methyl-1H-indazol-5-yl)methylidene]-3-oxobutanenitrile (Example 2A) and 7.27 g (60.7 mmol) 3-amino-4,4-difluorobut-2-enenitrile [obtainable by Thorpe reaction of acetonitrile with 2,2-difluoroacetonitrile, cf. Org. React. 15, 1 (1967), ibid. 31, 1 (1984)] in 2-propanol (20 ml) and triethylamine (0.21 ml) was stirred at reflux temperature overnight. After cooling, the precipitate was collected by filtration and washed twice with cold 2-propanol. The crude product was purified by silica gel chromatography (tert-butyl methyl ether/ethanol gradient, final mixture 94:6 v/v) to yield 0.36 g (7% of th.) of the racemic title compound as a pale yellow solid.

LC-MS (method 2): $R_t$=0.91 min; MS (ESIpos): m/z=326 (M+H)$^+$ $^1$H-NMR (400 MHz, DMSO-d$_6$): δ=12.73 (s, 1H), 10.07 (s, 1H), 7.58 (s, 1H), 7.53 (d, 1H), 7.29 (d, 1H), 6.81 (t, 1H, $^2J_{HF}$=52.09 Hz), 4.70 (s, 1H), 2.54 (s, 3H), 2.12 (s, 3H) ppm.

Example 2 and Example 3

2-(Difluoromethyl)-6-methyl-4-(3-methyl-1H-indazol-5-yl)-1,4-dihydropyridine-3,5-dicarbonitrile (Enantiomer 1 and 2)

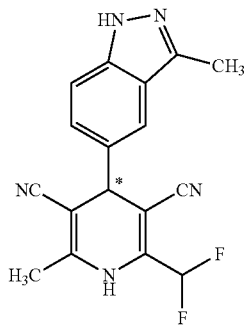

The racemic compound from Example 1 was separated into the enantiomers by HPLC chromatography on a chiral phase [column: Daicel Chiralpak IB-H, 5 μm, 250 mm×20 mm; eluent: tert-butyl methyl ether/acetonitrile+0.2% diethylamine 90:10 v/v; flow rate: 15 ml/min; temperature: 30° C.; UV detection: 220 nm]:

Example 2

Enantiomer 1

>99% ee $R_t$=4.78 min [column: Daicel Chiralpak IB-H, 5 μm, 250 mm×4.6 mm; eluent: tert-butyl methyl ether/acetonitrile 90:10; flow rate: 1 ml/min; temperature: 40° C.; UV detection: 220 nm].

DSC: melting point 305° C., ΔH 57 J/g

FT-IR (solid): 3345, 3194, 3095, 2201 (CN), 1665, 1630, 1530, 1512, 1388, 1328, 1291, 1279, 1134, 1095, 1065, 1050, 1022, 995, 844, 770, 737, 666 cm$^{-1}$.

Example 3

Enantiomer 2

>98% ee $R_t$=5.78 min [column: Daicel Chiralpak IB-H, 5 μm, 250 mm×4.6 mm; eluent: tert-butyl methyl ether/acetonitrile 90:10; flow rate: 1 ml/min; temperature: 40° C.; UV detection: 220 nm].

DSC: melting point 307° C., ΔH 48 J/g

FT-IR (solid): 3344, 3193, 3094, 2202 (CN), 1666, 1630, 1530, 1512, 1383, 1329, 1291, 1279, 1134, 1095, 1065, 1050, 1022, 995, 844, 771, 737, 666 cm$^{-1}$.

Example 4 rac-2-Methyl-4-(3-methyl-1H-indazol-5-yl)-6-(trifluoromethyl)-1,4-dihydropyridine-3,5-dicarbonitrile

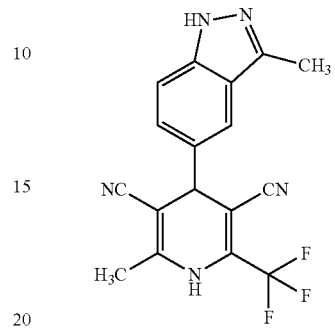

A suspension of 5.4 g (24.0 mmol) (2E)-2-[(3-methyl-1H-indazol-5-yl)methylidene]-3-oxobutanenitrile (Example 2A) and 13.05 g (95.9 mmol) 3-amino-4,4,4-trifluorobut-2-enenitrile [preparation: A. W. Lutz, U.S. Pat. No. 3,635,977; C. G. Krespan, *J. Org. Chem.* 34, 42 (1969)] in 2-propanol (27 ml) and triethylamine (0.33 ml) was stirred at reflux temperature for 15 h. After cooling, the precipitate was collected by filtration, washed twice with cold 2-propanol and dried under high vacuum to yield 5.98 g (72% of th.) of the racemic title compound as a tan solid.

LC-MS (method 4): $R_t$=0.87 min; MS (ESIpos): m/z=344 (M+H)$^+$ $^1$H-NMR (400 MHz, DMSO-d$_6$): δ=12.75 (s, 1H), 10.27 (s, 1H), 7.62 (s, 1H), 7.54 (d, 1H), 7.31 (d, 1H), 4.79 (s, 1H), 2.49 (s, 3H), 2.13 (s, 3H) ppm.

Example 5 and Example 6

2-Methyl-4-(3-methyl-1H-indazol-5-yl)-6-(trifluoromethyl)-1,4-dihydropyridine-3,5-dicarbonitrile (Enantiomer 1 and 2)

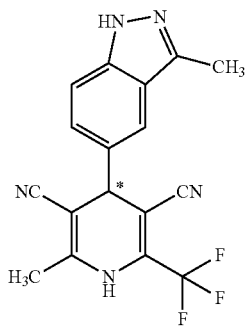 [SMILES: CC1=C(C#N)C(c2ccc3[nH]nc(C)c3c2)C(C#N)=C(C(F)(F)F)N1]

The racemic compound from Example 4 was separated into the enantiomers by HPLC chromatography on a chiral phase [column: chiral silica gel phase based on the selector poly(N-methacryloyl-L-leucine-tert-butylamide) (cf. EP 0 379 917, EP 0 780 408), 10 μm, 600 mm×40 mm; 1 g racemate dissolved in 40 ml acetonitrile with 2.5 ml diethylamine; eluent: ethyl acetate; flow rate: 90 ml/min; temperature: 20° C.; UV detection: 265 nm]:

Example 5

Enantiomer 1

>99% ee $R_t$=4.81 min [column: chiral silica gel phase based on the selector poly(N-methacryloyl-L-leucine-tert-butylamide), 10 μm, 250 mm×4.6 mm; eluent: ethyl acetate; flow rate: 1.5 ml/min; temperature: 25° C.; UV detection: 260 nm].

DSC: melting point 298° C., ΔH 43 J/g (followed by broad exothermic decomposition)

FT-IR (solid): 3306, 3105, 2210 (CN), 1669, 1547, 1364, 1328, 1285, 1203, 1181, 1150, 1099, 992, 880, 786, 674 cm$^{-1}$.

Example 6

Enantiomer 2

>99% ee $R_t$=7.57 min [column: chiral silica gel phase based on the selector poly(N-methacryloyl-L-leucine-tert-butylamide), 10 μm, 250 mm×4.6 mm; eluent: ethyl acetate; flow rate: 1.5 ml/min; temperature: 25° C.; UV detection: 260 nm].

DSC: melting point 315° C., ΔH 130 J/g (followed by broad exothermic decomposition)

FT-IR (solid): 3304, 3105, 2210 (CN), 1669, 1546, 1364, 1328, 1285, 1203, 1181, 1149, 1099, 992, 880, 786, 674 cm$^{-1}$.

Single crystal X-ray structural analysis revealed an S-configuration at the C*-atom for this enantiomer.

Example 7 rac-2-(Difluoromethyl)-4-(6-fluoro-3-methyl-1H-indazol-5-yl)-6-methyl-1,4-dihydropyridine-3,5-dicarbonitrile

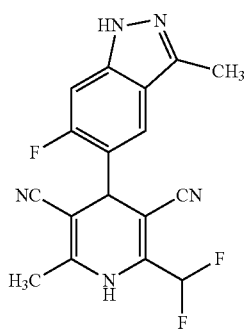 [SMILES: CC1=C(C#N)C(c2cc3c(C)n[nH]c3cc2F)C(C#N)=C(C(F)F)N1]

Following the procedure described for Example 1, 100 mg (0.411 mmol) (2E)-2-[(6-fluoro-3-methyl-1H-indazol-5-yl)methylidene]-3-oxobutanenitrile (Example 4A) were treated with 3-amino-4,4-difluorobut-2-enenitrile. The crude product was purified by preparative RP-HPLC (aceto-nitrile/water+0.1% TFA gradient, final mixture 90:10 v/v) to yield 50 mg (35% of th.) of the racemic title compound.

LC-MS (method 4): $R_t$=0.83 min; MS (ESIpos): m/z=344 (M+H)$^+$ $^1$H-NMR (400 MHz, DMSO-d$_6$): δ=12.82 (br. s, 1H), 10.10 (s, 1H), 7.69 (d, 1H), 7.32 (d, 1H), 6.81 (t, 1H, $^2J_{HF}$=52.09 Hz), 4.93 (s, 1H), 2.54 (s, 3H), 2.10 (s, 3H) ppm.

Example 8 and Example 9

2-(Difluoromethyl)-4-(6-fluoro-3-methyl-1H-indazol-5-yl)-6-methyl-1,4-dihydropyridine-3,5-dicarbonitrile (Enantiomer 1 and 2)

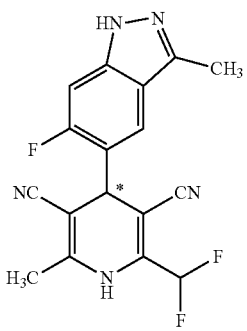 [SMILES: CC1=C(C#N)C(c2cc3c(C)n[nH]c3cc2F)C(C#N)=C(C(F)F)N1]

The racemic compound from Example 7 was separated into the enantiomers by HPLC chromatography on a chiral phase [column: chiral silica gel phase based on the selector poly(N-methacryloyl-L-leucine-[(+)-3S-pinanylmethyl]amide) (cf. EP 0 379 917, EP 0 780 408), 10 μm, 250 mm×20 mm; eluent: tert-butyl methyl ether+0.2% diethylamine/methanol 95:5 v/v; flow rate: 15 ml/min; temperature: 30° C.; UV detection: 220 nm]:

Example 8

Enantiomer 1

>99% ee $R_t$=5.33 min [column: chiral silica gel phase based on the selector poly(N-methacryloyl-L-leucine-[(+)-3S-pinanylmethyl]amide), 10 μm, 250 mm×4.6 mm; eluent: tert-butyl methyl ether+0.2% diethylamine/methanol 95:5; flow rate: 1 ml/min; temperature: 25° C.; UV detection: 235 nm].

Example 9

Enantiomer 2

>98% ee $R_t$=7.02 min [column: chiral silica gel phase based on the selector poly(N-methacryloyl-L-leucine-[(+)-3S-pinanylmethyl]amide), 10 μm, 250 mm×4.6 mm; eluent: tert-butyl methyl ether+0.2% diethylamine/methanol 95:5; flow rate: 1 ml/min; temperature: 25° C.; UV detection: 235 nm].

Example 10 rac-4-(6-Fluoro-3-methyl-1H-indazol-5-yl)-2-methyl-6-(trifluoromethyl)-1,4-dihydropyridine-3,5-dicarbonitrile

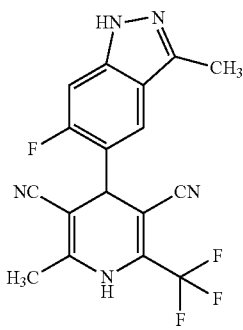 [SMILES: CC1=C(C#N)C(c2cc3c(C)n[nH]c3cc2F)C(C#N)=C(C(F)(F)F)N1]

Following the procedure described for Example 4, 250 mg (0.411 mmol) (2E)-2-[(6-fluoro-3-methyl-1H-indazol-5-yl)methylidene]-3-oxobutanenitrile (Example 4A) were treated with 3-amino-4,4,4-trifluorobut-2-enenitrile. The crude product was purified by preparative RP-HPLC (aceto-nitrile/water gradient, final mixture 90:10 v/v) to yield 159 mg (42% of th.) of the racemic title compound.

LC-MS (method 2): $R_t$=0.98 min; MS (ESIpos): m/z=362 (M+H)$^+$ $^1$H-NMR (400 MHz, DMSO-$d_6$): δ=12.34 (br. s, 1H), 10.31 (s, 1H), 7.74 (d, 1H), 7.35 (d, 1H), 5.01 (s, 1H), 2.54 (s, 3H), 2.11 (s, 3H) ppm.

Example 11 and Example 12

4-(6-Fluoro-3-methyl-1H-indazol-5-yl)-2-methyl-6-(trifluoromethyl)-1,4-dihydropyridine-3,5-dicarbonitrile (Enantiomer 1 and 2)

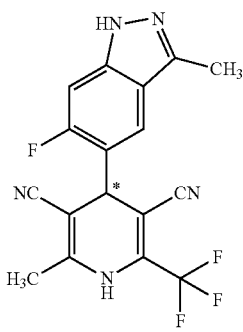 [SMILES: CC1=C(C#N)C(c2cc3c(C)n[nH]c3cc2F)C(C#N)=C(C(F)(F)F)N1]

The racemic compound from Example 10 was separated into the enantiomers by HPLC chromatography on a chiral phase [column: Daicel Chiralpak 1B-H, 5 μm, 250 mm×20 mm; eluent: tert-butyl methyl ether/acetonitrile+0.2% diethylamine 90:10 v/v; flow rate: 15 ml/min; temperature: 30° C.; UV detection: 220 nm]:

Example 11

Enantiomer 1

>99% ee $R_t$=3.90 min [column: chiral silica gel phase based on the selector poly(N-methacryloyl-L-leucine-[(+)-3S-pinanylmethyl]amide), 10 μm, 250 mm×4.6 mm; eluent: tert-butyl methyl ether+0.2% diethylamine/methanol 95:5; flow rate: 1 ml/min; temperature: 25° C.; UV detection: 235 nm].

Example 12

Enantiomer 2

>98% ee $R_t$=6.35 min [column: chiral silica gel phase based on the selector poly(N-methacryloyl-L-leucine-[(+)-3S-pinanylmethyl]amide), 10 μm, 250 mm×4.6 mm; eluent: tert-butyl methyl ether+0.2% diethylamine/methanol 95:5; flow rate: 1 ml/min; temperature: 25° C.; UV detection: 235 nm].

Example 13

2,6-Bis(difluoromethyl)-4-(3-methyl-1H-indazol-5-yl)-1,4-dihydropyridine-3,5-dicarbonitrile

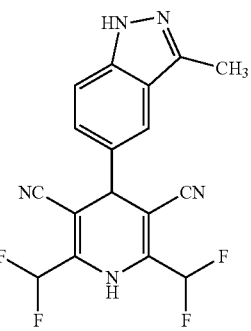

A solution of 80 mg (0.50 mmol) 3-methyl-1H-indazole-5-carbaldehyde (Example 1A) and 130 mg (1.10 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] in acetic acid (0.5 ml) containing powdered 4 Å molecular sieve was heated to reflux temperature for 3.5 h. After cooling, the reaction mixture was diluted with methanol/dichloromethane and filtered. The filtrate was evaporated, and the residue was purified by preparative RP-HPLC (acetonitrile/water+0.1% TFA gradient) yielding 61 mg (34% of th.) of the title compound.

LC-MS (method 2): $R_t$=0.94 min; MS (ESIpos): m/z=362 (M+H)$^+$ $^1$H-NMR (400 MHz, DMSO-$d_6$): δ=12.80 (br. s, 1H), 10.70 (s, 1H), 7.62 (s, 1H), 7.58 (d, 1H), 7.30 (d, 1H), 6.84 (t, 2H), 4.89 (s, 1H), 2.49 (s, 3H) ppm.

FT-IR (solid): 3348, 3116, 2805, 2209 (CN), 1668, 1630, 1548, 1513, 1417, 1339, 1275, 1259, 1131, 1058, 1043, 996, 890, 856, 776, 666 cm$^{-1}$.

DSC: melting point 289° C., ΔH 27 J/g (followed by broad exothermic decomposition).

Example 14

2,6-Bis(difluoromethyl)-4-(6-fluoro-3-methyl-1H-indazol-5-yl)-1,4-dihydropyridine-3,5-dicarbonitrile

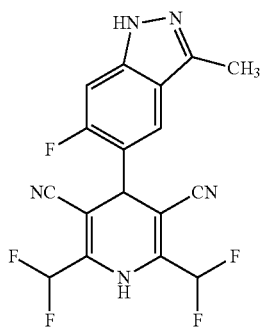 [SMILES: Cc1n[nH]c2cc(F)c(C3C(C#N)=C(C(F)F)NC(C(F)F)=C3C#N)cc12]

A solution of 100 mg (0.56 mmol) 6-fluoro-3-methyl-1H-indazole-5-carbaldehyde (Example 3A) and 146 mg (1.24 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] in acetic acid (0.54 ml) containing powdered 4 Å molecular sieve was heated to reflux temperature for 5 h. After cooling, the reaction mixture was diluted with THF and filtered. The filtrate was directly purified by preparative RP-HPLC (acetonitrile/water+0.1% TFA gradient) yielding 136 mg (64% of th.) of the title compound.

LC-MS (method 4): $R_t$=0.86 min; MS (ESIpos): m/z=380 (M+H)$^+$ $^1$H-NMR (400 MHz, DMSO-d$_6$): δ=12.89 (br. s, 1H), 10.73 (s, 1H), 7.76 (d, 1H), 7.38 (d, 1H), 6.82 (t, 2H), 5.12 (s, 1H), 2.49 (s, 3H) ppm.

FT-IR (solid): 3140, 2360, 2216 (CN), 1634, 1515, 1393, 1266, 1144, 1052, 1009, 893, 837, 742 cm$^{-1}$.

DSC: melting point 282° C., ΔH 138 J/g.

Example 15

2,6-Bis(difluoromethyl)-4-(6-fluoro-1H-indazol-5-yl)-1,4-dihydropyridine-3,5-dicarbonitrile

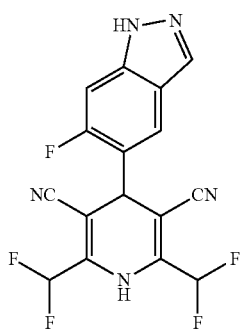 [SMILES: N#CC1=C(C(F)F)NC(C(F)F)=C(C#N)C1c1cc2cn[nH]c2cc1F]

A solution of 150 mg (0.55 mmol) 6-fluoro-1H-indazole-5-carbaldehyde (Example 5A) and 142 mg (1.21 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] in acetic acid (0.5 ml) containing powdered 4 Å molecular sieve was heated to reflux temperature for 5 h. After cooling, the reaction mixture was diluted with THF and filtered. The filtrate was directly purified by preparative RP-HPLC (acetonitrile/water+0.1% TFA gradient) yielding 147 mg (72% of th.) of the title compound.

LC-MS (method 4): $R_t$=0.83 min; MS (ESIpos): m/z=366 (M+H)$^+$ $^1$H-NMR (400 MHz, DMSO-d$_6$): δ=12.80 (br. s, 1H), 10.76 (s, 1H), 8.20 (s, 1H), 7.83 (d, 1H), 7.48 (d, 1H), 6.82 (t, 2H), 5.15 (s, 1H) ppm.

Example 16 rac-2-(Difluoromethyl)-4-(6-fluoro-1H-indazol-5-yl)-6-methyl-1,4-dihydropyridine-3,5-dicarbonitrile

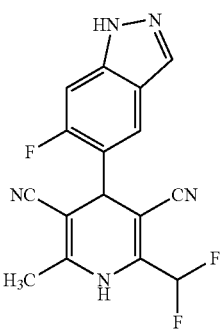 [SMILES: CC1=C(C#N)C(c2cc3cn[nH]c3cc2F)C(C#N)=C(C(F)F)N1]

A suspension of 200 mg (0.87 mmol) (2E)-2-[(6-fluoro-1H-indazol-5-yl)methylidene]-3-oxobutane-nitrite (Example 6A) and 419 mg (3.49 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] in 2-propanol (1 ml) was stirred at reflux temperature overnight. After cooling, the mixture was concentrated under reduced pressure, and the residue was suspended in p-xylene (3 ml). Small amounts of p-toluenesulfonic acid and powdered 4 Å molecular sieve were added, and the mixture was stirred at reflux temperature for 16 h. Upon cooling, the mixture was diluted with aceto-nitrile and filtered. The filtrate was concentrated under reduced pressure, and the crude product was purified by preparative RP-HPLC (acetonitrile/water gradient, final mixture 9:1 v/v) to yield 81 mg (28% of th.) of the racemic title compound as a pale yellow solid.

LC-MS (method 2): $R_t$=0.89 min; MS (ESIpos): m/z=330 (M+H)$^+$ $^1$H-NMR (400 MHz, DMSO-d$_6$): δ=13.24 (s, 1H), 10.14 (s, 1H), 8.15 (s, 1H), 7.79 (d, 1H), 7.42 (d, 1H), 6.82 (t, 1H, $^2J_{HF}$=51.84 Hz), 4.95 (s, 1H), 2.11 (s, 3H) ppm.

Example 17 and Example 18

2-(Difluoromethyl)-4-(6-fluoro-1H-indazol-5-yl)-6-methyl-1,4-dihydropyridine-3,5-dicarbonitrile (Enantiomer 1 and 2)

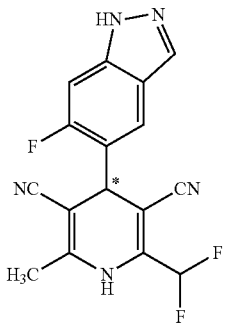 [SMILES: CC1=C(C#N)C(c2cc3cn[nH]c3cc2F)C(C#N)=C(C(F)F)N1]

The racemic compound from Example 16 was separated into the enantiomers by HPLC chromatography on a chiral phase [column: Daicel Chiralpak IB-H, 5 μm, 250 mm×20 mm; eluent: tert-butyl methyl ether/acetonitrile 90:10 v/v; flow rate: 15 ml/min; temperature: 30° C.; UV detection: 220 nm]:

Example 17

Enantiomer 1

>99% ee
$R_t$=6.15 min [column: Daicel Chiralpak IB-H, 5 μm, 250 mm×4.6 mm; eluent: tert-butyl methyl ether/acetonitrile 90:10; flow rate: 1 ml/min; temperature: 40° C.; UV detection: 220 nm].

Example 18

Enantiomer 2

>98.5% ee
$R_t$=7.88 min [column: Daicel Chiralpak IB-H, 5 μm, 250 mm×4.6 mm; eluent: tert-butyl methyl ether/acetonitrile 90:10; flow rate: 1 ml/min; temperature: 40° C.; UV detection: 220 nm].

Example 19 rac-4-(6-Fluoro-1H-indazol-5-yl)-2-methyl-6-(trifluoromethyl)-1,4-dihydropyridine-3,5-dicarbonitrile

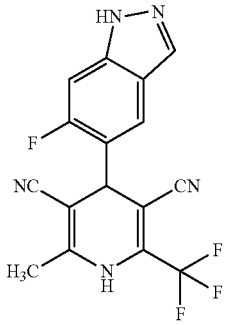 [SMILES: CC1=C(C#N)C(c2cc3cn[nH]c3cc2F)C(C#N)=C(C(F)(F)F)N1]

Following the procedure described for Example 4, 200 mg (0.87 mmol) (2E)-2-[(6-fluoro-1H-indazol-5-yl)methylidene]-3-oxobutanenitrile (Example 6A) were treated with 3-amino-4,4,4-trifluorobut-2-enenitrile. The crude product was purified by preparative RP-HPLC (acetonitrile/water gradient, final mixture 90:10 v/v) to yield 115 mg (40% of th.) of the racemic title compound.

LC-MS (method 3): $R_t$=1.83 min; MS (ESIpos): m/z=348 (M+H)$^+$ $^1$H-NMR (400 MHz, DMSO-d$_6$): δ=13.27 (s, 1H), 10.34 (s, 1H), 8.16 (s, 1H), 7.84 (d, 1H), 7.44 (d, 1H), 5.03 (s, 1H), 2.12 (s, 3H) ppm.

Example 20 rac-4-(1H-Indazol-5-yl)-2-methyl-6-(trifluoromethyl)-1,4-dihydropyridine-3,5-dicarbonitrile

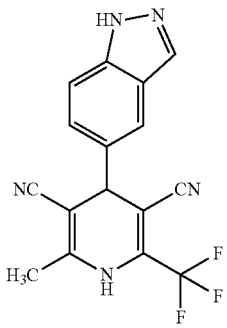 [SMILES: CC1=C(C#N)C(c2ccc3[nH]ncc3c2)C(C#N)=C(C(F)(F)F)N1]

A mixture of 250 mg (1.71 mmol) 1H-indazole-5-carbaldehyde, 180 mg (1.71 mmol) sodium 1-cyanoprop-1-en-2-olate and 931 mg (6.84 mmol) 3-amino-4,4,4-trifluorobut-2-enenitrile [preparation: A. W. Lutz, U.S. Pat. No. 3,635,977; C. G. Krespan, J. Org. Chem. 34, 42 (1969)] in 1-pentanol (2.5 ml) and acetic acid (0.15 ml) was heated to 105° C. overnight. After cooling, the reaction mixture was diluted with THF and directly purified by preparative RP-HPLC (acetonitrile/water+0.1% TFA gradient) yielding 131 mg (23% of th.) of the racemic title compound.

LC-MS (method 2): $R_t$=0.93 min; MS (ESIpos): m/z=330 (M+H)$^+$ $^1$H-NMR (400 MHz, DMSO-d$_6$): δ=13.19 (br. s, 1H), 10.30 (s, 1H), 8.12 (s, 1H), 7.71 (s, 1H), 7.63 (d, 1H), 7.32 (d, 1H), 4.79 (s, 1H), 2.12 (s, 3H) ppm.

Example 21 and Example 22

4-(1H-Indazol-5-yl)-2-methyl-6-(trifluoromethyl)-1,4-dihydropyridine-3,5-dicarbonitrile (Enantiomer 1 and 2)

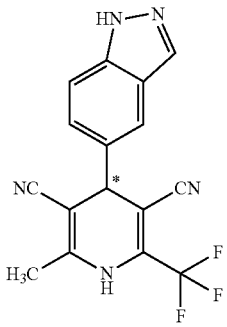 [SMILES: CC1=C(C#N)C(c2ccc3[nH]ncc3c2)C(C#N)=C(C(F)(F)F)N1]

The racemic compound from Example 20 (90 mg) was separated into the enantiomers by HPLC chromatography on a chiral phase [column: chiral silica gel phase based on the selector poly(N-methacryloyl-L-leucine-tert-butylamide)

(cf. EP 0 379 917, EP 0 780 408), 10 μm, 240 mm×20 mm; eluent: iso-hexane/ethyl acetate 10:90 v/v; flow rate: 40 mL/min; temperature: 25° C.; UV detection: 260 nm]:

Example 21

Enantiomer 1

Yield: 24 mg (99.5% ee)

$R_t$=5.54 min [column: chiral silica gel phase based on the selector poly(N-methacryloyl-L-leucine-tert-butylamide), 250 mm×4 mm; eluent: iso-hexane/ethyl acetate 20:80 v/v; flow rate: 2 mL/min; UV detection: 260 nm].

Example 22

Enantiomer 2

Yield: 21 mg (99% ee)

$R_t$=8.67 min [column: chiral silica gel phase based on the selector poly(N-methacryloyl-L-leucine-tert-butylamide), 250 mm×4 mm; eluent: iso-hexane/ethyl acetate 20:80 v/v; flow rate: 2 ml/min; UV detection: 260 nm].

Example 23 rac-4-(3-Ethyl-1H-indazol-5-yl)-2-methyl-6-(trifluoromethyl)-1,4-dihydropyridine-3,5-dicarbonitrile

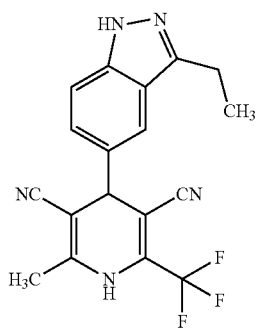 [SMILES: CCc1n[nH]c2ccc(C3C(C#N)=C(C)NC(C(F)(F)F)=C3C#N)cc12]

A suspension of 300 mg (1.25 mmol) (2E)-2-[(3-ethyl-1H-indazol-5-yl)methylidene]-3-oxobutanenitrile (Example 11A) and 853 mg (6.27 mmol) 3-amino-4,4,4-trifluorobut-2-enenitrile [preparation: A. W. Lutz, U.S. Pat. No. 3,635,977; C. G. Krespan, *J. Org. Chem.* 34, 42 (1969)] in ethanol/2-propanol (8:1 v/v, 1.0 ml) was stirred at reflux temperature for 24 h. After cooling, the reaction mixture was concentrated under reduced pressure, and the residue was purified by preparative RP-HPLC (acetonitrile/water+0.1% TFA gradient) to yield 59 mg (13% of th.) of the racemic title compound.

LC-MS (method 4): $R_t$=0.91 min; MS (ESIpos): m/z=358 (M+H)⁺

¹H-NMR (400 MHz, DMSO-d₆): δ=12.74 (s, 1H), 10.25 (s, 1H), 7.62 (s, 1H), 7.55 (d, 1H), 7.30 (d, 1H), 4.78 (s, 1H), 2.93 (q, 2H), 2.13 (s, 3H), 1.32 (t, 3H) ppm.

Example 24

2,6-Bis(difluoromethyl)-4-(1H-indazol-5-yl)-1,4-dihydropyridine-3,5-dicarbonitrile

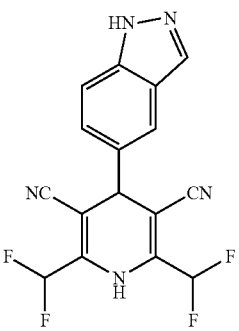 [SMILES: N#CC1=C(C(F)F)NC(C(F)F)=C(C#N)C1c1ccc2[nH]ncc2c1]

A mixture of 80 mg (0.55 mmol) 1H-indazole-5-carbaldehyde, 142 mg (1.21 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 1 (1984)] and a trace amount of powdered 4 Å molecular sieve in acetic acid (0.53 ml) was heated to reflux temperature for 5 h. After cooling, the reaction mixture was diluted with THF and filtered. The filtrate was directly purified by preparative RP-HPLC (acetonitrile/water+0.1% TFA gradient) yielding 95 mg (48% of th.) of the title compound.

LC-MS (method 4): $R_t$=0.81 min; MS (ESIpos): m/z=348 (M+H)⁺

¹H-NMR (400 MHz, DMSO-d₆): δ=13.21 (br. s, 1H), 10.70 (s, 1H), 8.16 (s, 1H), 7.72 (s, 1H), 7.66 (d, 1H), 7.32 (d, 1H), 6.82 (t, 2H), 4.90 (s, 1H) ppm.

Example 25

2,6-Bis(difluoromethyl)-4-(3-ethyl-1H-indazol-5-yl)-1,4-dihydropyridine-3,5-dicarbonitrile

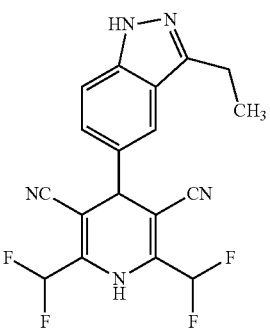 [SMILES: CCc1n[nH]c2ccc(C3C(C#N)=C(C(F)F)NC(C(F)F)=C3C#N)cc12]

A mixture of 80 mg (0.46 mmol) 3-ethyl-1H-indazole-5-carbaldehyde (Example 10A), 119 mg (1.21 mmol) 3-amino- 4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] and a trace amount of powdered 4 Å molecular sieve in acetic acid (0.44 ml) was heated to reflux temperature for 4 h. After cooling, the reaction mixture was diluted with THF/methanol and filtered. The filtrate was purified twice by preparative RP-HPLC (acetonitrile/water+0.1% TFA gradient) yielding 99 mg (57% of th.) of the title compound.

LC-MS (method 4): $R_t$=0.88 min; MS (ESIpos): m/z=376 (M+H)$^+$ $^1$H-NMR (400 MHz, DMSO-$d_6$): δ=12.79 (br. s, 1H), 10.69 (s, 1H), 7.68 (s, 1H), 7.59 (d, 1H), 7.30 (d, 1H), 6.84 (t, 2H), 4.88 (s, 1H), 2.93 (q, 2H), 1.32 (t, 3H) ppm.

Example 26

4-(3-Methyl-1H-indazol-5-yl)-2,6-bis(trifluoromethyl)-1,4-dihydropyridine-3,5-dicarbonitrile

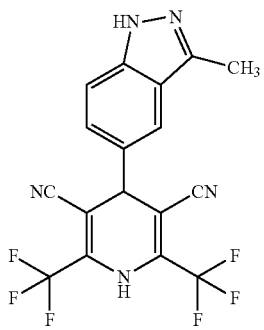 [SMILES: Cc1n[nH]c2ccc(C3C(C#N)=C(C(F)(F)F)NC(C(F)(F)F)=C3C#N)cc12]

A mixture of 50 mg (0.31 mmol) 3-methyl-1H-indazole-5-carbaldehyde (Example 1A), 106 mg (0.78 mmol) 3-amino-4,4,4-trifluorobut-2-enenitrile [preparation: A. W. Lutz, U.S. Pat. No. 3,635,977; C. G. Krespan, *J. Org. Chem.* 34, 42 (1969)] and a trace amount of powdered 4 Å molecular sieve in acetic acid (0.30 ml) was heated to reflux temperature for 2 h. After cooling, the reaction mixture was diluted with methanol/dichloromethane and filtered. The filtrate was evaporated, and the residue was purified by preparative RP-HPLC (acetonitrile/water+0.1% TFA gradient) to give 19 mg (15% of th.) of the title compound.

LC-MS (method 4): $R_t$=0.92 min; MS (ESIpos): m/z=398 (M+H)$^+$ $^1$H-NMR (400 MHz, DMSO-$d_6$): δ=12.80 (br. s, 1H), 7.62 (s, 1H), 7.59 (d, 1H), 7.31 (d, 1H), 4.87 (s, 1H), 2.49 (s, 3H) ppm.

The following compounds were prepared in analogy to the procedure described in Example 26; purification was carried out by preparative RP-HPLC using a methanol/water+0.1% TFA gradient:

| Example | Name/Structure (yield) | Analytical data |
|---|---|---|
| 27 | 4-(6-Fluoro-1H-indazol-5-yl)-2,6-bis(trifluoromethyl)-1,4-dihydropyridine-3,5-dicarbonitrile<br><br>(4% of th.) | LC-MS (method 2): $R_t$ = 1.05 min; m/z = 402 (M + H)$^+$ $^1$H-NMR (400 MHz, DMSO-$d_6$): δ = 12.9 (br. s, 1H), 8.18 (s, 1H), 7.75 (m, 1H), 7.42 (d, 1H), 1H) ppm. |
| 28 | 4-(3-Ethyl-1H-indazol-5-yl)-2,6-bis(trifluoromethyl)-1,4-dihydropyridine-3,5-dicarbonitrile<br><br>(29% of th.) | LC-MS (method 4): $R_t$ = 0.96 min; m/z = 412 (M + H)$^+$ $^1$H-NMR (400 MHz, DMSO-$d_6$): δ = 12.8 (br. s, 1H), 7.63 (s, 1H), 7.57 (d, 1H), 7.30 (d, 1H), 4.85 (s, 1H), 2.93 (q, 2H), 1.32 (t, 3H) ppm. |
| 29 | 4-(6-Fluoro-3-methyl-1H-indazol-5-yl)-2,6-bis(trifluoromethyl)-1,4-dihydropyridine-3,5-dicarbonitrile<br><br>(35% of th.) | LC-MS (method 4): $R_t$ = 0.93 min; m/z = 416 (M + H)$^+$ $^1$H-NMR (400 MHz, DMSO-$d_6$): δ = 12.8 (br. s, 1H), 7.75 (d, 1H), 7.38 (d, 1H), 5.14 (s, 1H), 2.49 (s, 3H) ppm. |

Example 30 rac-2-(1,1-Difluoropropyl)-6-methyl-4-(3-methyl-1H-indazol-5-yl)-1,4-dihydropyridine-3,5-dicarbonitrile

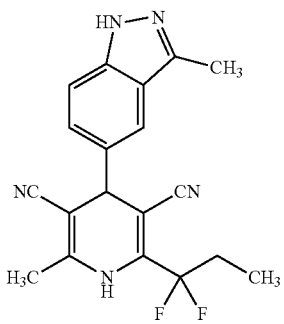 [SMILES: CCC(F)(F)C1=C(C#N)C(c2ccc3[nH]nc(C)c3c2)C(C#N)=C(C)N1]

A solution of 113 mg (0.50 mmol) (2E)-2-[(3-methyl-1H-indazol-5-yl)methylidene]-3-oxobutanenitrile (Example 2A) and 432 mg (0.50 mmol based on 17% purity) 4,4-difluoro-3-oxohexanenitrile (Example 13A) in 2-propanol (334 µl) and acetic acid (170 µl) was treated with 116 mg (1.5 mmol) ammonium acetate and stirred for 20 min at 90° C. under microwave conditions. After cooling, the mixture was concentrated under reduced pressure, and the residue was suspended in p-xylene (1.5 ml). Small amounts of p-toluenesulfonic acid and powdered 4 Å molecular sieve were added, and the mixture was stirred at reflux temperature for 48 h. Upon cooling, the mixture was diluted with acetonitrile, filtered and concentrated under reduced pressure. The crude product was purified by preparative RP-HPLC (acetonitrile/water gradient, final mixture 9:1 v/v) followed by preparative thin layer silica gel chromatography (toluene/ethanol 5:1 v/v) to yield 7.2 mg (4% of th.) of the racemic title compound as a pale yellow solid.

LC-MS (method 2): $R_t$=1.00 min; MS (ESIpos): m/z=354 $(M+H)^+$ $^1$H-NMR (400 MHz, DMSO-$d_6$): δ=12.73 (s, 1H), 9.68 (s, 1H), 7.57 (s, 1H), 7.53 (d, 1H), 7.28 (d, 1H), 4.64 (s, 1H), 2.54 (s, 3H), 2.24 (m, 2H), 2.13 (s, 3H), 1.00 (t, 3H) ppm.

Example 31

2-Hydroxy-N,N,N-trimethylethanaminium 3,5-dicyano-2-methyl-4-(3-methyl-1H-indazol-5-yl)-6-(difluoromethyl)-4H-pyridin-1-ide (Enantiomer 1)

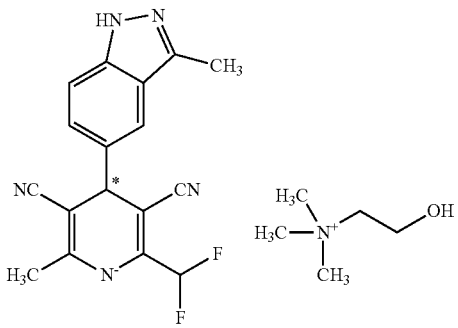

To a suspension of 75 mg (0.23 mmol) 2-(difluoromethyl)-6-methyl-4-(3-methyl-1H-indazol-5-yl)-1,4-dihydropyridine-3,5-dicarbonitrile (Enantiomer 1; Example 2) in ethanol (1.6 ml) under argon atmosphere was added 32.6 µl (0.23 mmol) 2-hydroxy-N,N,N-trimethylethanaminium hydrogencarbonate solution (choline bicarbonate, 80% in water), and the mixture was stirred at reflux temperature for 1 h. Subsequently, the solution was evaporated, and the residue was dried in vacuo. The precipitate was stirred in 1.5 ml THF for 3 days and then centrifuged to yield 56 mg (56% of th.) of the title compound as a yellow solid.

LC-MS (method 4): $R_t$=0.82 min; MS (ESIpos): m/z=326 $(M-C_5H_{14}NO+2H)^+$ $^1$H-NMR (400 MHz, DMSO-$d_6$): δ=12.55 (s, 1H), 7.43 (d, 1H), 7.32 (s, 1H), 7.27 (d, 1H), 6.12 (t, 1H, $^2J_{HF}$=55.0 Hz), 5.30 (s, 1H), 4.42 (s, 1H), 3.82 (m, 2H), 3.38 (m, 2H), 3.10 (s, 9H), 2.46 (s, 3H), 1.88 (s, 3H) ppm.

FT-IR (solid): 3329, 3012, 2169 (CN), 1583, 1513, 1378, 1350, 1281, 1238, 1130, 1089, 1030, 1002, 952, 936, 884, 870, 853, 764, 735 cm$^{-1}$.

DSC: 182° C. (broad exothermic decomposition), ΔH−884 J/g.

Example 32

2-Hydroxy-N,N,N-trimethylethanaminium 3,5-dicyano-2-methyl-4-(3-methyl-1H-indazol-5-yl)-6-(difluoromethyl)-4H-pyridin-1-ide (Enantiomer 2)

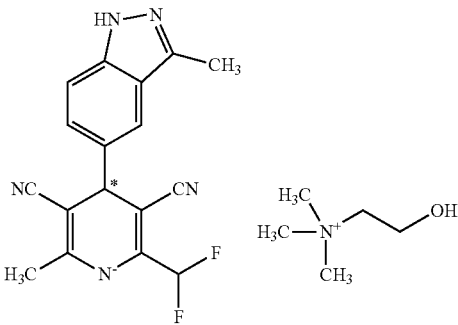

To a suspension of 67 mg (0.21 mmol) 2-(difluoromethyl)-6-methyl-4-(3-methyl-1H-indazol-5-yl)-1,4-dihydropyridine-3,5-dicarbonitrile (Enantiomer 2; Example 3) in ethanol (1.4 ml) under argon atmosphere was added 28.9 µl (0.21 mmol) 2-hydroxy-N,N,N-trimethylethanaminium hydrogencarbonate solution (choline bicarbonate, 80% in water), and the mixture was stirred at reflux temperature for 1 h. Subsequently, the solution was evaporated, and the residue was dried in vacuo. The precipitate was stirred in 1.5 ml THF for 3 days and then centrifuged to yield 48 mg (54% of th.) of the title compound as a yellow solid.

LC-MS (method 4): $R_t$=0.82 min; MS (ESIpos): m/z=326 $(M-C_5H_{14}NO+2H)^+$ $^1$H-NMR (400 MHz, DMSO-$d_6$): δ=12.55 (s, 1H), 7.43 (d, 1H), 7.32 (s, 1H), 7.27 (d, 1H), 6.12 (t, 1H, $^2J_{HF}$=55.0 Hz), 5.30 (s, 1H), 4.42 (s, 1H), 3.82 (m, 2H), 3.38 (m, 2H), 3.10 (s, 9H), 2.46 (s, 3H), 1.88 (s, 3H) ppm.

FT-IR (solid): 3328, 2861, 2169 (CN), 1591, 1512, 1378, 1350, 1280, 1238, 1129, 1089, 1031, 1002, 952, 936, 884, 869, 853, 764, 735 cm$^{-1}$.

DSC: 176° C. (broad exothermic decomposition), ΔH−747 J/g.

Example 33

2-Hydroxy-N,N,N-trimethylethanaminium (4S)-3,5-dicyano-2-methyl-4-(3-methyl-1H-indazol-5-yl)-6-(trifluoromethyl)-4H-pyridin-1-ide

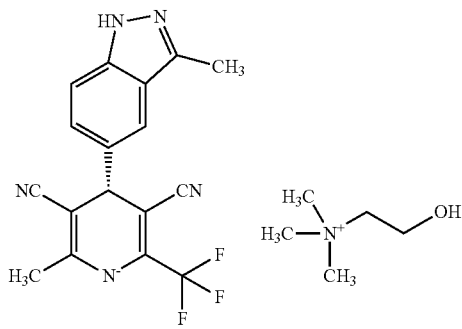

To a suspension of 101 mg (0.30 mmol) (4S)-2-methyl-4-(3-methyl-1H-indazol-5-yl)-6-(trifluoromethyl)-1,4-dihydropyridine-3,5-dicarbonitrile (Example 6) in ethanol (2.43 ml) under argon atmosphere was added 52 μl (0.30 mmol) 2-hydroxy-N,N,N-trimethylethanaminium hydrogencarbonate solution (choline bicarbonate, 80% in water), and the mixture was stirred at reflux temperature for 40 min. Subsequently, the solution was evaporated, and the residue was dried in vacuo. The precipitate was stirred in 1.5 ml THF/pentane (9:1 v/v) for 7 days and then centrifuged to yield 70 mg (51% of th.) of the title compound as a solid.

LC-MS (method 3): $R_t$=1.81 min; MS (ESIpos): m/z=344 $(M-C_5H_{14}NO+2H)^+$ $^1$H-NMR (400 MHz, DMSO-$d_6$): δ=12.58 (s, 1H), 7.44 (d, 1H), 7.32 (s, 1H), 7.25 (d, 1H), 5.29 (s, 1H), 4.42 (s, 1H), 3.85-3.80 (m, 2H), 3.39-3.35 (m, 2H), 3.10 (s, 9H), 2.46 (s, 3H), 1.90 (s, 3H) ppm.

FT-IR (solid): 3418, 3097, 3021, 2865, 2175 (CN), 1592, 1516, 1486, 1376, 1330, 1283, 1210, 1170, 1150, 1120, 1088, 998, 956, 935, 888, 864, 844, 819, 764, 732, 710, 685 cm$^{-1}$.

DSC: 182° C. (broad exothermic decomposition), ΔH−814 J/g.

Example 34

Sodium (4S)-3,5-dicyano-2-methyl-4-(3-methyl-1H-indazol-5-yl)-6-(trifluoromethyl)-4H-pyridin-1-ide

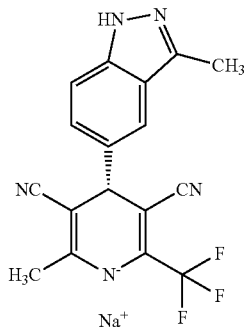 [SMILES: CC1=C(C#N)[C@H](c2ccc3[nH]nc(C)c3c2)C(C#N)=C(C(F)(F)F)[N-]1 ; [Na+]]

To a suspension of 200 mg (0.583 mmol) (4S)-2-methyl-4-(3-methyl-1H-indazol-5-yl)-6-(trifluoromethyl)-1,4-dihydropyridine-3,5-dicarbonitrile (Example 6) in THF (6 ml) under argon atmosphere was added 612 μl (0.612 mmol) 1 N aqueous sodium hydroxide solution, and the mixture was stirred under a weak argon stream for 3 days at room temperature. The product was crystallized by stirring the resulting solid in water under a slight argon stream for another 3 days to dryness, yielding 212 mg (100% of th.) of the title compound as a solid.

LC-MS (method 4): $R_t$=0.86 min; MS (ESIpos): m/z=344 $(M-Na+2H)^+$ $^1$H-NMR (400 MHz, DMSO-$d_6$): δ=12.58 (s, 1H), 7.44 (d, 1H), 7.32 (s, 1H), 7.25 (d, 1H), 4.42 (s, 1H), 2.46 (s, 3H), 1.90 (s, 3H) ppm.

FT-IR (solid): 3302, 2870, 2183 (CN), 1631, 1587, 1508, 1438, 1378, 1329, 1284, 1205, 1180, 1150, 1125, 1055, 995, 880, 821, 786, 764, 729, 675, 657 cm$^{-1}$.

DSC: 227° C. (exothermic decomposition), ΔH−150 J/g.

Example 35

Potassium (4S)-3,5-dicyano-2-methyl-4-(3-methyl-1H-indazol-5-yl)-6-(trifluoromethyl)-4H-pyridin-1-ide

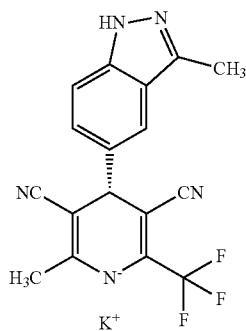 [SMILES: CC1=C(C#N)[C@H](c2ccc3[nH]nc(C)c3c2)C(C#N)=C(C(F)(F)F)[N-]1 ; [K+]]

To a suspension of 60 mg (0.175 mmol) (4S)-2-methyl-4-(3-methyl-1H-indazol-5-yl)-6-(trifluoromethyl)-1,4-dihydropyridine-3,5-dicarbonitrile (Example 6) in THF (6 ml) under argon atmosphere was added 175 μl (0.175 mmol) 1 N aqueous potassium hydroxide solution, and the mixture was stirred under a weak argon stream for 5 days at room temperature. The resulting precipitate was dried in vacuo to yield 66 mg (100% of th.) of the title compound as a solid.

LC-MS (method 4): $R_t$=0.87 min; MS (ESIpos): m/z=344 $(M-K+2H)^+$ $^1$H-NMR (400 MHz, DMSO-$d_6$): δ=12.58 (s, 1H), 7.44 (d, 1H), 7.32 (s, 1H), 7.25 (d, 1H), 4.42 (s, 1H), 2.46 (s, 3H), 1.90 (s, 3H) ppm.

FT-IR (solid): 3296, 2876, 2173 (CN), 1631, 1588, 1510, 1436, 1379, 1330, 1285, 1205, 1180, 1149, 1124, 1054, 996, 882, 821, 786, 764, 729, 704, 665 cm$^{-1}$.

DSC: 199° C. (exothermic decomposition), ΔH−93 J/g.

Example 36

2-Hydroxy-N,N,N-trimethylethanaminium (4R)-3,5-dicyano-2-methyl-4-(3-methyl-1H-indazol-5-yl)-6-(trifluoromethyl)-4H-pyridin-1-ide

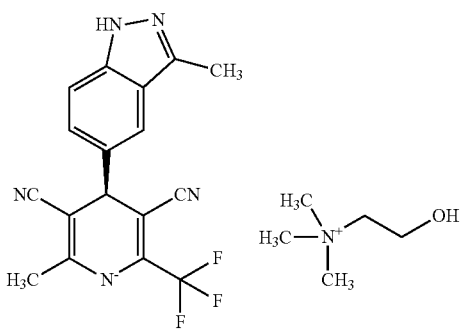

To a suspension of 100 mg (0.29 mmol) (4R)-2-methyl-4-(3-methyl-1H-indazol-5-yl)-6-(trifluoromethyl)-1,4-dihydropyridine-3,5-dicarbonitrile (Example 5) in ethanol (2.1 ml) under argon atmosphere was added 41 μl (0.29 mmol) 2-hydroxy-N,N,N-trimethylethanaminium hydrogencarbonate solution (choline bicarbonate, 80% in water), and the mixture was stirred at reflux temperature for 40 min. Subsequently, the solution was evaporated, and the residue was dried in vacuo. The precipitate was stirred in 1.5 ml THF/pentane (9:1 v/v) for 3 days and then centrifuged to yield 84 mg (64% of th.) of the title compound as a solid.

LC-MS (method 4): $R_t$=0.88 min; MS (ESIpos): m/z=344 (M-$C_5H_{14}$NO+2H)$^+$ $^1$H-NMR (400 MHz, DMSO-$d_6$): δ=12.56 (s, 1H), 7.44 (d, 1H), 7.34 (s, 1H), 7.26 (d, 1H), 5.29 (s, 1H), 4.42 (s, 1H), 3.85-3.80 (m, 2H), 3.39-3.35 (m, 2H), 3.10 (s, 9H), 2.46 (s, 3H), 1.90 (s, 3H) ppm.

FT-IR (solid): 3419, 2867, 2175 (CN), 1592, 1517, 1487, 1377, 1330, 1285, 1212, 1171, 1150, 1122, 1095, 999, 956, 935, 864, 819, 764, 732, 710, 688 cm$^{-1}$.

DSC: 197° C. (broad exothermic decomposition), ΔH–744 J/g.

Example 37

Sodium (4R)-3,5-dicyano-2-methyl-4-(3-methyl-1H-indazol-5-yl)-6-(trifluoromethyl)-4H-pyridin-1-ide

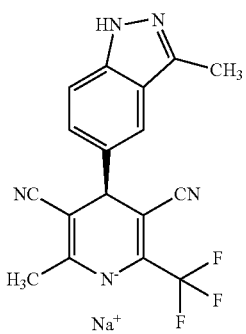

To a suspension of 41 mg (0.12 mmol) (4R)-2-methyl-4-(3-methyl-1H-indazol-5-yl)-6-(trifluoromethyl)-1,4-dihydropyridine-3,5-dicarbonitrile (Example 5) in THF (1 ml) under argon atmosphere was added 131 μl (0.13 mmol) 1 N aqueous sodium hydroxide solution, and the mixture was stirred under a weak argon stream for 5 days at room temperature. The resulting precipitate was dried in vacuo to yield 44 mg (100% of th.) of the title compound as a solid.

LC-MS (method 4): $R_t$=0.86 min; MS (ESIpos): m/z=344 (M-Na+2H)$^+$ $^1$H-NMR (400 MHz, DMSO-$d_6$): δ=12.58 (s, 1H), 7.44 (d, 1H), 7.32 (s, 1H), 7.25 (d, 1H), 4.42 (s, 1H), 2.46 (s, 3H), 1.90 (s, 3H) ppm.

Example 38

Potassium (4R)-3,5-dicyano-2-methyl-4-(3-methyl-1H-indazol-5-yl)-6-(trifluoromethyl)-4H-pyridin-1-ide

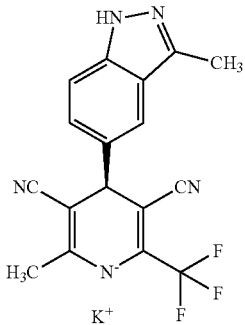 [SMILES: CC1=C(C#N)[C@@H](c2ccc3[nH]nc(C)c3c2)C(C#N)=C(C(F)(F)F)[N-]1 ; [K+]]

To a suspension of 39 mg (0.11 mmol) (4R)-2-methyl-4-(3-methyl-1H-indazol-5-yl)-6-(trifluoromethyl)-1,4-dihydropyridine-3,5-dicarbonitrile (Example 5) in THF (2 ml) under argon atmosphere was added 126 μl (0.12 mmol) 1 N aqueous potassium hydroxide solution, and the mixture was stirred under a weak argon stream for 5 days at room temperature. The resulting precipitate was dried in vacuo to yield 44 mg (100% of th.) of the title compound as a solid.

LC-MS (method 4): $R_t$=0.87 min; MS (ESIpos): m/z=344 (M-K+2H)$^+$ $^1$H-NMR (400 MHz, DMSO-$d_6$): δ=12.58 (s, 1H), 7.44 (d, 1H), 7.32 (s, 1H), 7.25 (d, 1H), 4.42 (s, 1H), 2.46 (s, 3H), 1.90 (s, 3H) ppm.

Example 39

Sodium 3,5-dicyano-2,6-bis(difluoromethyl)-4-(6-fluoro-3-methyl-1H-indazol-5-yl)-4H-pyridin-1-ide

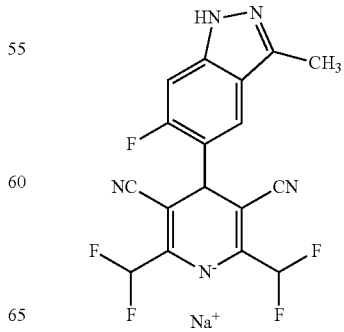

To a suspension of 100 mg (0.28 mmol) 2,6-bis(difluoromethyl)-4-(6-fluoro-3-methyl-1H-indazol-5-yl)-1,4-dihydropyridine-3,5-dicarbonitrile (Example 14) in ethanol (0.25 ml) under argon atmosphere was added 290 µl (0.29 mmol) 1 N aqueous sodium hydroxide solution, and the mixture was stirred under a weak argon stream for 4 days at room temperature. The resulting precipitate was dried in vacuo to yield 110 mg (100% of th.) of the title compound as a solid.

LC-MS (method 3): $R_t$=1.82 min; MS (ESIpos): m/z=380 (M-Na+2H)$^+$ $^1$H-NMR (400 MHz, DMSO-d$_6$): δ=12.69 (s, 1H), 7.46 (d, 1H), 7.21 (d, 1H), 6.22 (t, 2H), 4.82 (s, 1H), 2.44 (s, 3H) ppm.

Example 40

2-Hydroxy-N,N,N-trimethylethanaminium 3,5-dicyano-2,6-bis(difluoromethyl)-4-(6-fluoro-3-methyl-1H-indazol-5-yl)-4H-pyridin-1-ide

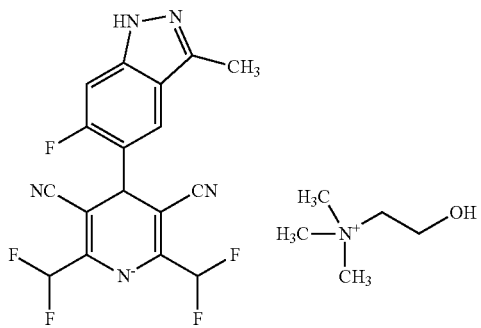

To a suspension of 100 mg (0.26 mmol) 2,6-bis(difluoromethyl)-4-(6-fluoro-3-methyl-1H-indazol-5-yl)-1,4-dihydropyridine-3,5-dicarbonitrile (Example 14) in ethanol (1.52 ml) under argon atmosphere was added 47 µl (0.26 mmol) 2-hydroxy-N,N,N-trimethylethanaminium hydrogencarbonate solution (choline bicarbonate, 80% in water), and the mixture was stirred at reflux temperature for 1 h.

Subsequently, a weak argon stream was led over the solution mixture. The resulting precipitate was dried in vacuo to yield 130 mg (100% of th.) of the title compound as a solid.

LC-MS (method 4): $R_t$=0.86 min; MS (ESIpos): m/z=380 (M-C$_5$H$_{14}$NO+2H)$^+$ $^1$H-NMR (400 MHz, DMSO-d$_6$): 67 =12.69 (br. s, 1H), 7.46 (d, 1H), 7.21 (d, 1H), 6.22 (t, 2H), 5.82 (br. s, 1H), 4.82 (s, 1H), 3.82 (br. s, 2H), 3.40 (br. s, 2H), 3.11 (s, 9H), 2.44 (s, 3H) ppm.

FT-IR (solid): 3388, 2870, 2183 (CN), 1633, 1595, 1525, 1487, 1390, 1360, 1285, 1270, 1123, 1030, 952, 822, 703 cm$^{-1}$.

DSC: 171° C. (broad exothermic decomposition), ΔH–573 J/g.

Example 41

2-Hydroxy-N,N,N-trimethylethanaminium 3,5-dicyano-2,6-bis(difluoromethyl)-4-(3-methyl-1H-indazol-5-yl)-4H-pyridin-1-ide

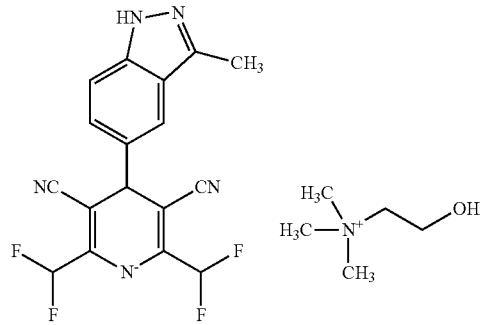

To a suspension of 80 mg (0.22 mmol) 2,6-bis(difluoromethyl)-4-(3-methyl-1H-indazol-5-yl)-1,4-dihydropyridine-3,5-dicarbonitrile (Example 13) in ethanol (1.52 ml) under argon atmosphere was added 31 µl (0.22 mmol) 2-hydroxy-N,N,N-trimethylethanaminium hydrogencarbonate solution (choline bicarbonate, 80% in water), and the mixture was stirred at reflux temperature for 1 h. Subsequently, a weak argon stream was led over the solution mixture. The crude product was treated with THF (1.5 ml) and stirred for 2 days under argon. The resulting precipitate was collected by centrifugation and dried in vacuo to yield 57 mg (54% of th.) of the title compound as a yellow solid.

LC-MS (method 4): $R_t$=0.85 min; MS (ESIpos): m/z=361 (M-C$_5$H$_{14}$NO+2H)$^+$ $^1$H-NMR (400 MHz, DMSO-d$_6$): δ=12.6 (s, 1H), 7.47 (d, 1H), 7.39 (s, 1H), 7.26 (d, 1H), 6.22 (t, 2H), 5.26 (t, 1H), 4.52 (s, 1H), 3.82 (br. m, 2H), 3.40 (m, 2H), 3.11 (s, 9H), 2.46 (s, 3H) ppm.

FT-IR (solid): 3422, 2360, 2183 (CN), 1601, 1524, 1387, 1364, 1275, 1270, 1131, 1032, 1009, 958, 893, 866, 769 cm$^{-1}$.

DSC: 161° C. (broad exothermic decomposition), ΔH–779 J/g.

Example 42 rac-1,2-Dimethyl-4-(3-methyl-1H-indazol-5-yl)-6-(trifluoromethyl)-1,4-dihydropyridine-3,5-dicarbonitrile

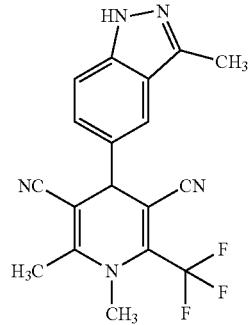 [SMILES: CC1=C(C#N)C(c2ccc3[nH]nc(C)c3c2)C(C#N)=C(C(F)(F)F)N1C]

A solution of 375 mg (1.09 mmol) 2-methyl-4-(3-methyl-1H-indazol-5-yl)-6-(trifluoromethyl)-1,4-dihydropyridine-3,5-dicarbonitrile (Example 4) in DMF (11.5 ml) was cooled to 0° C. 534 mg (1.64 mmol) caesium carbonate were added at this temperature, and after 15 min 48 µl (0.77 mmol) methyl iodide were added dropwise at room temperature. After stirring overnight at rt, additional methyl iodide (20 µl) and a small amount of caesium carbonate were added, and the reaction mixture was stirred at rt for further 3 h before water and methanol were added. The resulting solution was directly purified by preparative RP-HPLC (acetonitrile/water+0.1% TFA gradient) to give 75 mg (19% of th.) of the racemic title compound.

LC-MS (method 4): R$_t$=0.94 min; MS (ESIpos): m/z=358 (M+H)$^+$ $^1$H-NMR (400 MHz, DMSO-d$_6$): δ=12.77 (br. s, 1H), 7.58 (s, 1H), 7.54 (d, 1H), 7.28 (d, 1H), 4.69 (s, 1H), 3.30 (s, 3H), 2.49 (s, 3H), 2.32 (s, 3H) ppm.

Example 43 and Example 44

1,2-Dimethyl-4-(3-methyl-1H-indazol-5-yl)-6-(trifluoromethyl)-1,4-dihydropyridine-3,5-dicarbonitrile (Enantiomer 1 and 2)

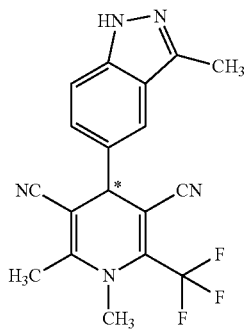 [SMILES: CC1=C(C#N)C(c2ccc3[nH]nc(C)c3c2)C(C#N)=C(C(F)(F)F)N1C]

The racemic compound from Example 42 (74 mg) was separated into the enantiomers by HPLC chromatography on a chiral phase [column: Daicel Chiralpak AD-H, 5 µm, 250 mm×20 mm; eluent: iso-hexane/ethanol 75:25 v/v; flow rate: 15 ml/min; temperature: 30° C.; UV detection: 220 nm]:

Example 43

Enantiomer 1

Yield: 21 mg (chemical purity >99%, >99% ee)

R$_t$=6.09 min [column: Daicel Chiralpak AD-H, 5 µm, 250 mm×4.6 mm; eluent: iso-hexane/ethanol 70:30+0.2% TFA+1% water; flow rate: 1 ml/min; temperature: 35° C.; UV detection: 220 nm].

Example 44

Enantiomer 2

Yield: 20 mg (chemical purity >99%, >95% ee)

R$_t$=6.65 min [column: Daicel Chiralpak AD-H, 5 µm, 250 mm×4.6 mm; eluent: iso-hexane/ethanol 70:30+0.2% TFA+1% water; flow rate: 1 ml/min; temperature: 35° C.; UV detection: 220 nm].

Example 45

2,6-Bis(difluoromethyl)-1-methyl-4-(3-methyl-1H-indazol-5-yl)-1,4-dihydropyridine-3,5-dicarbonitrile

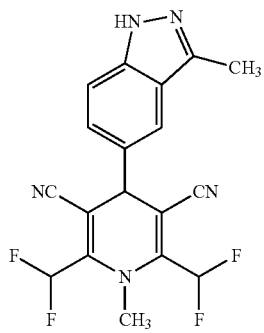 [SMILES: Cc1n[nH]c2ccc(C3C(C#N)=C(C(F)F)N(C)C(C(F)F)=C3C#N)cc12]

A solution of 100 mg (0.277 mmol) 2,6-bis(difluoromethyl)-4-(3-methyl-1H-indazol-5-yl)-1,4-dihydropyridine-3,5-dicarbonitrile (Example 13) in DMF (1.5 ml) was cooled to 0° C., and 108 mg (0.33 mmol) caesium carbonate were added at this temperature. After stirring for 30 min, 21 µl (0.33 mmol) methyl iodide were added dropwise at room temperature, and the mixture was stirred at rt overnight. After this, additional methyl iodide (20 µl) was added, and stirring at rt was continued for further 48 h. The reaction mixture was then filtered, and the filtrate was directly purified by preparative RP-HPLC (acetonitrile/water+0.1% TFA isocratic 40:60 v/v) to give 12 mg (11% of th.) of the title compound.

LC-MS (method 4): R$_t$=0.96 min; MS (ESIpos): m/z=376 (M+H)$^+$ $^1$H-NMR (400 MHz, DMSO-d$_6$): δ=12.8 (br. s, 1H), 7.62 (s, 1H), 7.57 (d, 1H), 7.30 (d, 1H), 7.11 (t, 2H), 4.83 (s, 1H), 3.40 (s, 3H), 2.50 (s, 3H) ppm.

Example 46 rac-2-(Difluoromethyl)-4-(3-methyl-1H-indazol-5-yl)-6-(trifluoromethyl)-1,4-dihydropyridine-3,5-dicarbonitrile

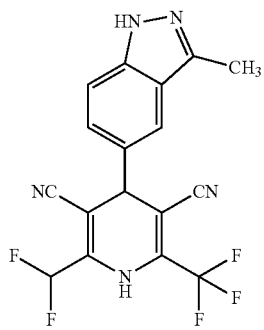 [SMILES: Cc1n[nH]c2ccc(C3C(C#N)=C(C(F)F)NC(C(F)(F)F)=C3C#N)cc12]

A mixture of 150 mg (0.936 mmol) 3-methyl-1H-indazole-5-carbaldehyde (Example 1A), 273 mg (1.03 mmol) 4,4- difluoro-3-oxobutanenitrile (Example 14A), 0.067 ml (1.17 mmol) acetic acid and 9.3 µl (0.094 mmol) piperidine in dry dichloromethane (4 ml) containing 4 Å molecular sieve was stirred under reflux for 12 h. Then, the mixture was filtered, and the filtrate was concentrated under reduced pressure. The residue was dissolved in 2-propanol (2 ml) and acetic acid (1 ml) under argon, and 510 mg (3.75 mmol) 3-amino-4,4,4-trifluorobut-2-enenitrile [preparation: A. W. Lutz, U.S. Pat. No. 3,635,977; C. G. Krespan, *J. Org. Chem.* 34, 42 (1969)] were added. The solution was stirred under reflux for 6 h. Upon cooling, the mixture was evaporated to dryness, and the residue was treated with toluene (4 ml) containing a small amount of p-toluenesulfonic acid. The mixture was stirred under reflux for further 12 h. Upon cooling, the mixture was evaporated to dryness again, and the residue was dissolved in ethyl acetate. The organic phase was washed with saturated aqueous sodium hydrogencarbonate solution and with water, dried over sodium sulfate, and concentrated under reduced pressure. The residue was purified by preparative RP-HPLC (methanol/water+0.1% TFA gradient) to yield 39 mg (11% of th.) of the racemic title compound.

LC-MS (method 3): $R_t$=1.90 min; MS (ESIpos): m/z=380 (M+H)$^+$ $^1$H-NMR (400 MHz, DMSO-d$_6$): δ=12.82 (br. s, 1H), 10.93 (br. s, 1H), 7.68 (s, 1H), 7.58 (d, 1H), 7.33 (d, 1H), 6.81 (t, 1H, $^2J_{HF}$=52 Hz), 4.96 (s, 1H), 2.50 (s, 3H) ppm.

B. EVALUATION OF BIOLOGICAL ACTIVITY

Demonstration of the activity of the compounds of the present invention may be accomplished through in vitro, ex vivo, and in vivo assays that are well known in the art. For example, to demonstrate the activity of the compounds of the present invention, the following assays may be used:

c-Met Receptor Tyrosine Kinase Activity Assay (NADH Read-Out):

Recombinant human c-Met protein (Invitrogen, Carlsbad, Calif., USA) is used. As substrate for the kinase reaction the peptide KKKSPGEYVNIEFG (JPT, Germany) is used. For the assay, 1 µL of a 51-fold concentrated solution of the test compound in DMSO is pipetted into a white 384-well microtiter plate (Greiner Bio-One, Frickenhausen, Germany). 25 µL of a solution of c-Met (final concentration 30 nM) and pyruvate kinase/lactate dehydrogenase (Roche Diagnostics, Mannheim, Germany; final concentration 8 mg/L) in assay buffer [3-(N-morpholino)propanesulfonic acid (MOPS), 50 mM, pH 7; MgCl$_2$, 10 mM; bovine serum albumin (BSA), 0.01%; Triton X 100, 0.01%; DTT, 2 mM] are added, and the mixture is incubated for 5 min at room temperature. Then, the kinase reaction is started by the addition of 25 µL of a solution of adenosine triphosphate (ATP, final concentration 30 µM), substrate (final concentration 100 µM), nicotinamide adenine dinucleo-tide (NADH, final concentration 50 µM) and dithiothreitol (DTT, final concentration 2 mM) in assay buffer, and the resulting mixture is incubated for a reaction time of 100 min at 32° C.

Subsequently, the amount of phosphorylated substrate is evaluated by measurement of the decrease of NADH fluorescence. Therefore, the fluorescence emissions at 465 nm after excitation at 340 nm is measured in a fluorescence reader, e.g. Tecan Ultra (Tecan, Männedorf, Switzerland). The data are normalised (enzyme reaction without inhibitor=0% inhibition; all other assay components but no enzyme=100% inhibition). Normally, test compounds are tested on the same microtiter plate at 9 different concentrations in the range of 10 µM to 1 nM (10 µM, 3.1 µM, 1.0 µM, 0.3 µM, 0.1 µM, 0.03 µM, 0.01 µM, 0.003 µM, 0.001 µM; dilution series prepared before the assay at the level of the 51-fold concentrated stock solutions by serial 1:3 dilutions) in duplicate for each concentration, and IC$_{50}$ values are calculated using an inhouse software.

Some representative IC$_{50}$ values are listed in Table 1 below together with corresponding data for a structurally related, non-fluorinated compound from prior art (cf. WO 2008/071451):

TABLE 1

| Example No. | IC$_{50}$ [µM] |
| --- | --- |
| 2 | 0.006 |
| 3 | 0.006 |
| 5 | 0.012 |
| 6 | 0.012 |
| 8 | 0.009 |
| 14 | 0.026 |
| 17 | 0.011 |
| 20 | 0.027 |
| 24 | 0.028 |
| 30 | 0.021 |
| 43 | 0.009 |
| 44 | 0.008 |
| Synthetic Example 4 in WO 2008/071451 | 0.008 | c-Met Receptor Tyrosine Kinase Homogeneous Time-Resolved Fluorescence Assay (Alternative Format):

The N-terminally His6-tagged recombinant kinase domain of the human c-Met (amino acids 960-1390), expressed in insect cells (SF21) and purified by Ni-NTA affinity chromatography and consecutive size exclusion chromatography (Superdex 200), is used. Alternatively, commercially available c-Met (Millipore) can be used. As substrate for the kinase reaction, the biotinylated poly-Glu, Tyr (4:1) copolymer (#61GTOBLC, Cis Biointernational, Marcoule, France) is used.

For the assay, 50 mL of a 100-fold concentrated solution of the test compound in DMSO is pipetted into a black low-volume 384-well microtiter plate (Greiner Bio-One, Frickenhausen, Germany). 2 µL of a solution of c-Met in assay buffer [25 mM Hepes/NaOH, pH 7.5; 5 mM MgCl$_2$; 5 mM MnCl$_2$; 2 mM dithiothreitol; 0.1% (v/v) Tween 20 (Sigma); 0.1% (w/v) bovine serum albumin] are added, and the mixture is incubated for 15 min at 22° C. to allow pre-binding of the test compound to the enzyme before the start of the kinase reaction. Then, the kinase reaction is started by the addition of 3 µL of a solution of adenosine triphosphate (ATP, 16.7 µM; final concentration in the 5 µL assay volume is 10 µM) and substrate (2.27 µg/mL, final concentration in the 5 µL assay volume is 1.36 µg/mL ~30 nM) in assay buffer, and the resulting mixture is incubated for a reaction time of 30 min at 22° C. The concentration of c-Met in the assay is adjusted depending on the activity of the enzyme lot and is appropriately chosen to have the assay in the linear range; typical enzyme concentrations are in the range of about 0.03 nM (final concentration in the 5 µL assay volume). The reaction is stopped by the addition of 5 µL of a solution of HTRF detection reagents [40 nM streptavidine-X Lent and 2.4 nM PT66-Eu-chelate, an europium-chelate labelled anti-phosphotyrosine antibody (Perkin-Elmer)] in an aqueous EDTA solution [100 mM EDTA, 0.2% (w/v) bovine serum albumin in 50 mM HEPES/NaOH, pH 7.5].

The resulting mixture is incubated for 1 h at 22° C. to allow the binding of the biotinylated phosphorylated peptide to the streptavidine-XLent and the PT66-Eu-chelate. Subsequently, the amount of phosphorylated substrate is evaluated by measurement of the resonance energy transfer from the PT66-Euchelate to the streptavidine-XLent. Therefore, the fluorescence emissions at 620 nm and 665 nm after excitation at 350 nm are measured in an HTRF reader, e.g. Rubystar (BMG Lab-technologies, Offenburg, Germany) or Viewlux (Perkin-Elmer). The ratio of the emissions at 665 nm and at 622 nm is taken as the measure for the amount of phosphorylated substrate. The data are normalised (enzyme reaction without inhibitor=0% inhibition; all other assay components but no enzyme=100% inhibition). Normally, test compounds are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM; dilution series prepared before the assay at the level of the 100-fold concentrated stock solutions by serial 1:3 dilutions) in duplicate for each concentration, and $IC_{50}$ values are calculated by a 4-parameter-fit using an inhouse software.

Some representative $IC_{50}$ values are listed in Table 2 below together with corresponding data for a structurally related, non-fluorinated compound from prior art (cf. WO 2008/071451):

TABLE 2

| Example No. | $IC_{50}$ [µM] |
|---|---|
| 2 | 0.002 |
| 3 | 0.002 |
| 6 | 0.001 |
| 14 | 0.003 |
| 30 | 0.003 |
| Synthetic Example 4 in WO 2008/071451 | 0.002 |

Phospho-c-Met Assay:

This is a cell based, ELISA-like assay [Meso Scale Discovery (MSD), Gaithersburg, Md., USA] using MKN-45 tumor cells (gastric carcinoma, purchased from ATCC) without growth factor stimulation. The cells are plated in full growth media (10 000 cells/well) in 96-well plates on day one. On day two, after a two-hour drug treatment in serum-free media, cells are washed and then lysed (60 µl/well using MSD recommended lysis buffer) and frozen at −80° C. Also on day two, non-specific antibody-binding sites on the MSD phospho-Met plates are blocked with MSD Blocking Solution A overnight at 4° C. On day three, frozen lysates are thawed on ice, and 25 µl of lysate is transferred to the MSD phospho-Met plate, for 1 hour with shaking, after washing once with Tris-buffered saline+0.05% Tween 20 (TBST). After removing the unbound proteins, the Sulfa-TAG anti-Met antibody from MSD is added at a final concentration of 5 nM in antibody dilution buffer (following protocol of MSD) to the plate for 1 hour with shaking. The plate is then washed with TBST buffer three times before adding 1×MSD Read Buffer. The plate is then read on the MSD Discovery Workstation instrument. Raw data, including wells with 10 µM of a reference compound (minimum signal), and DMSO wells without any drug treatment (maximum signal), are entered into the Analyze 5 program for $IC_{50}$ value determinations.

Cellular Phospho-c-Met Assay:

Human gastric adenocarcinoma cells (MKN45, purchased from ATCC) seeded on 384-well microtiter plates (9000 cells/well) are incubated in 25 µl full growth media for 24 h at 37° C. with 5% $CO_2$. On day two, after a two-hour drug treatment in serum-reduced media containing 0.1% FCS, cells are washed and lysed. Lysates are transferred to BSA-blocked plates with prebound c-Met capture antibody [purchased from Mesoscale Discovery (MSD), Gaithersburg, Md., USA] for 1 hour with shaking, after washing once with Tris-buffered saline+0.05% Tween 20 (TBST). Following the MSD protocol, the Sulfa-TAG anti-phospho-c-Met detection antibody is added at a final concentration of 5 nM in antibody dilution buffer to the plate for 1 hour with shaking at RT. After washing the wells with Tris buffer, 1× reading buffer is added, and the plates are measured on the Sector Imager 6000 (purchased from Mesoscale). $IC_{50}$ values are calculated from dose-response curves using Marquardt-Levenberg-Fit.

In-Vitro Tumor Cell Proliferation Assay:

The adherent tumor cell proliferation assay used to test the compounds of the present invention involves a read-out called Cell Titre-Glo developed by Promega [B. A. Cunningham, "A Growing Issue: Cell Proliferation Assays. Modern kits ease quantification of cell growth", *The Scientist* 2001, 15 (13), 26; S. P. Crouch et al., "The use of ATP bioluminescence as a measure of cell proliferation and cytotoxicity", *Journal of Immunological Methods* 1993, 160, 81-88]. Generation of a luminescent signal corresponds to the amount of ATP present, which is directly proportional to the number of metabolically active (proliferating) cells.

H460 cells (lung carcinoma, purchased from ATCC) are plated in 96-well plates at 3000 cells/well in complete media with 10% fetal calf serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titre-Glo Luminescent® assay kit, the cells are lysed, and 100 µl of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$ values, a linear regression analysis can be used to determine the drug concentration which results in a 50% inhibition of cell proliferation using this assay format. This protocol can be applied to different cell lines of interest, which include, but not limited to, CAKI-1, MNK-45, GTL-16, HCC2998, K562, H441, K812, MEG01, SUP15 and HCT116.

C. EVALUATION OF PHARMACOKINETIC PROPERTIES

For evaluation of the pharmacokinetic (PK) profile of the compounds of the present invention, the following assays may be used:

Pharmacokinetics after Intravenous Administration of Test Compounds:

Male Wistar rats (Harlan Laboratories) are anesthetized and a catheter is inserted into the jugular vein of the rat. The next day, a defined dose of the test compound is administered as solution by injection into the tail vein. Blood samples are collected through the jugular catheter during the next 24 h (8-11 time points). Blood is centrifuged in heparin-tubes, and each plasma sample is treated with acetonitrile for protein precipitation. After centrifugation, the test compound in the supernatant is quantified using an LC-MS/MS method. The determined plasma concentrations are used for the calculation of pharmacokinetic parameters, such as AUC (area under the plasma concentration vs. time curve), $V_{ss}$ (volume of distribution under steady-state conditions), $C_{max}$ (highest test compound concentration observed in plasma following administration), $t_{1/2}$ (half-life) and CL (total clearance of the test compound from the plasma). For the calculation of the blood clearance, the blood to plasma partitioning is determined by incubation of the test compound in blood of rats. After separation of the plasma by centrifugation, the concentration in the plasma is determined by an LC-MS/MS method. Under the assumption that the test compound is completely absorbed, the theoretically maximum achievable bioavailability $F_{max,calc}$ is calculated by the equation $F_{max,calc}=[1-CL_{blood}/Q_h]*100$, wherein $CL_{blood}$ is the total blood clearance and $Q_h$ is the hepatic blood flow in rat of 4.2 L per h per kg.

Pharmacokinetics after Peroral Administration of Test Compounds:

Male Wistar rats (Harlan Laboratories) are anesthetized and a catheter is inserted into the jugular vein of the rat. The next day, a defined dose of the test compound is administered perorally. Blood samples are collected through the jugular catheter during the next 24 h (8-11 time points). Blood is centrifuged in heparin-tubes, and each plasma sample is treated with acetonitrile for protein precipitation. After centrifugation, the test compound in the supernatant is quantified using an LC-MS/MS method. The determined plasma concentrations are used for the determination of pharmacokinetic parameters, such as AUC (area under the plasma concentration vs. time curve), $C_{max}$ (highest test compound concentration observed in plasma following administration), $t_{1/2}$ (half-life) and F (bioavailability). The fraction of the dose absorbed ($f_{abs,calc}$) is calculated by the equation $f_{abs,calc}=[F/F_{max,calc}]*100$, wherein F is the determined bioavailability after peroral administration and $F_{max,calc}$ is the theoretically maximum achievable bioavailability considering the determined blood clearance and assuming that the test compound is completely absorbed.

Caco-2 Permeability Assay:

The in vitro permeation of a test compound across a Caco-2 cell monolayer is a well-established assay system to predict the permeability from the gastro-intestinal tract [cf. P. Artursson and J. Karlsson: Correlation between oral drug absorption in humans and apparent drug permeability coefficients in human intestinal epithelial (Caco-2) cells, *Biochem. Biophys.* 175 (3), 880-885 (1991)]. The permeability of the compounds of the present invention in such Caco-2 cells was determined as described below:

Human caco-2 cells (ACC No. 169, DSMZ, German Collection of Microorganisms and Cell Cultures, Braunschweig, Germany) are seeded on 24-well insert plates and are allowed to grow for 14-16 days. For permeability studies, the test compounds are dissolved in DMSO and diluted to the final test concentration of 2 μM with transport buffer [Hanks' Buffered Salt Solution, Gibco/Invitrogen, further supplemented with glucose (final concentration 19.9 mM) and HEPES (final concentration 9.8 mM)]. For determination of the apical to basolateral permeability ($P_{app}$A-B), the test compound solution is added to the apical side of the cell monolayer and transport buffer to the basolateral side of the monolayer; for determination of the basolateral to apical permeability ($P_{app}$B-A), the test compound solution is added to the basolateral side of the cell monolayer and transport buffer to the apical side of the monolayer. Samples are taken from the donor compartment at the beginning of the experiment to confirm mass balance. After an incubation of 2 h at 37° C., samples are taken from both compartments. Samples are analyzed by LC-MS/MS, and the apparent permeability coefficients are calculated. Lucifer Yellow permeability is assayed for each cell monolayer to ensure cell monolayer integrity, and the permeability of Atenolol (low permeability marker) and Sulfasalazine (marker for active excretion) is determined for each batch as quality control.

Representative results from these assays are listed in Table 3 below together with corresponding data for a structurally related, non-fluorinated compound from prior art (cf. WO 2008/071451):

TABLE 3

| Example No. | Caco-2 permeability $P_{app}$A-B [nm/s] | in vivo PK, rat i.v. | | in vivo PK, rat p.o. | | Fraction absorbed |
| --- | --- | --- | --- | --- | --- | --- |
| | | $CL_{blood}$ [L/h*kg] | $F_{max, calc}$ [%] | $AUC_{norm}$ [kg*h/L] | F [%] | $f_{abs, calc}$ [%] |
| 3 | 164 | 3.14 | 25 | 0.16 | 33 | 131 |
| 6 | 311 | 1.68 | 60 | 0.70 | 62 | 104 |
| 7 | 220 | 1.60 | 62 | 0.69 | 68 | 109 |
| 12 | 187 | 0.79 | 81 | 1.1 | 48 | 59 |
| 13 | 393 | 0.17 | 96 | 6.16 | 70 | 73 |
| 14 | 271 | 0.28 | 93 | 4.73 | 62 | 67 |
| 15 | 169 | 0.23 | 95 | 3.87 | 63 | 66 |
| 19 | 176 | 2.19 | 48 | 0.33 | 40 | 84 |
| Synthetic Example 4 in WO 2008/071451 | 124 | 3.25 | 23 | 0.052 | 9 | 39 |

[for the meaning and, where applicable, calculation of the PK parameters, see assay descriptions above; $AUC_{norm}$ = dose and body weight-normalized AUC value (AUC divided by dose per kg body weight)].

Further permeability data for compounds of the present invention are listed in Table 4 below:

TABLE 4

| Example No. | Caco-2 permeability $P_{app}$A-B [nm/s] |
| --- | --- |
| 16 | 226 |
| 20 | 200 |
| 24 | 202 |
| 25 | 290 |
| 26 | 348 |
| 30 | 220 |
| 42 | 388 |

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

D. EXAMPLES RELATING TO PHARMACEUTICAL COMPOSITIONS

Pharmaceutical compositions according to the present invention can be illustrated as follows:

Sterile i.v. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for i.v. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxy-methylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:

1. A compound of formula (I)

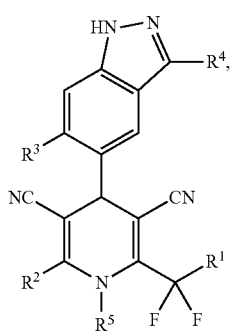

(I)

wherein
$R^1$ is hydrogen, fluoro, methyl or ethyl,
$R^2$ is methyl, difluoromethyl or trifluoromethyl,
$R^3$ is hydrogen or fluoro,
$R^4$ is hydrogen, methyl or ethyl,
and
$R^5$ is hydrogen or methyl,
or a pharmaceutically acceptable salt thereof.

2. The compound of formula (I) according to claim 1, wherein
$R^5$ is hydrogen,
or a pharmaceutically acceptable salt thereof.

3. The compound of formula (I) according to claim 1, wherein
$R^1$ is hydrogen or fluoro,
or a pharmaceutically acceptable salt thereof.

4. The compound of formula (I) according to claim 1, wherein
$R^1$ is hydrogen or fluoro,
$R^2$ is methyl or difluoromethyl,
$R^3$ is hydrogen or fluoro,
$R^4$ is hydrogen or methyl,
and
$R^5$ is hydrogen,
or a pharmaceutically acceptable salt thereof.

5. The compound of formula (I) according to claim 1, wherein the compound is selected from the group consisting of
rac-2-Methyl-4-(3-methyl-1H-indazol-5-yl)-6-(trifluoromethyl)-1,4-dihydropyridine-3,5-dicarbonitrile;
(4R)-2-Methyl-4-(3-methyl-1H-indazol-5-yl)-6-(trifluoromethyl)-1,4-dihydropyridine-3,5-dicarbonitrile;
(4S)-2-Methyl-4-(3-methyl-1H-indazol-5-yl)-6-(trifluoromethyl)-1,4-dihydropyridine-3,5-dicarbonitrile;
rac-2-(Difluoromethyl)-4-(6-fluoro-3-methyl-1H-indazol-5-yl)-6-methyl-1,4-dihydropyridine-3,5-dicarbonitrile;
(4R)-2-(Difluoromethyl)-4-(6-fluoro-3-methyl-1H-indazol-5-yl)-6-methyl-1,4-dihydropyridine-3,5-dicarbonitrile;
(4S)-2-(Difluoromethyl)-4-(6-fluoro-3-methyl-1H-indazol-5-yl)-6-methyl-1,4-dihydropyridine-3,5-dicarbonitrile;
2,6-Bis(difluoromethyl)-4-(3-methyl-1H-indazol-5-yl)-1,4-dihydropyridine-3,5-dicarbonitrile;
2,6-Bis(difluoromethyl)-4-(6-fluoro-3-methyl-1H-indazol-5-yl)-1,4-dihydropyridine-3,5-dicarbonitrile;
and
rac-4-(6-Fluoro-1H-indazol-5-yl)-2-methyl-6-(trifluoromethyl)-1,4-dihydropyridine-3,5-dicarbonitrile;
or a pharmaceutically acceptable salt thereof.

6. A salt of a compound of formula (I) according to claim 1, having a formula (I-A)

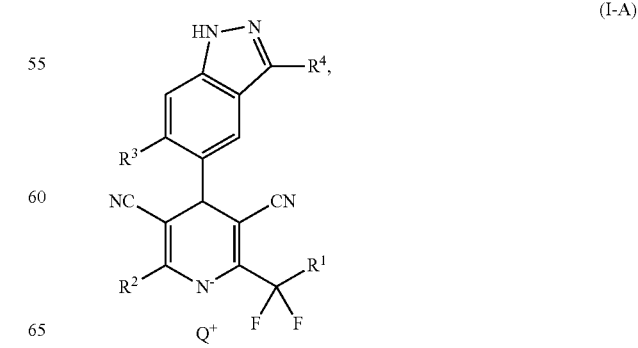

(I-A)

wherein $R^1$, $R^2$, $R^3$ and $R^4$ have the meanings defined in claim 1, and $Q^+$ is an alkali metal cation or a quaternary ammonium cation.

7. The salt of formula (I-A) according to claim 6, wherein $Q^+$ is a sodium or potassium cation or a 2-hydroxyethyltrimethyl ammonium (choline) cation.

8. The salt of formula (I-A) according to claim 6, wherein $Q^+$ is a 2-hydroxyethyltrimethyl ammonium (choline) cation.

9. A pharmaceutical composition comprising a compound as defined in claim 1, and a pharmaceutically acceptable excipient.

10. A pharmaceutical composition comprising a salt as defined in claim 6, and a pharmaceutically acceptable excipient.

* * * * *